United States Patent
Ohashi et al.

(10) Patent No.: US 11,998,390 B2
(45) Date of Patent: Jun. 4, 2024

(54) PIEZOELECTRIC ACTUATOR, ULTRASOUND ELEMENT, ULTRASOUND PROBE, ULTRASOUND DEVICE, AND ELECTRONIC DEVICE

(71) Applicant: Seiko Epson Corporation, Tokyo (JP)

(72) Inventors: Koji Ohashi, Matsumoto (JP); Chikara Kojima, Matsumoto (JP); Makoto Furuhata, Matsumoto (JP); Tomohide Onogi, Shiojiri (JP); Tomohiro Sayama, Matsumoto (JP)

(73) Assignee: SEIKO EPSON CORPORATION (JP)

( * ) Notice: Subject to any disclaimer, the term of this patent is extended or adjusted under 35 U.S.C. 154(b) by 36 days.

(21) Appl. No.: 17/456,387

(22) Filed: Nov. 24, 2021

(65) Prior Publication Data

US 2022/0160331 A1   May 26, 2022

(30) Foreign Application Priority Data

Nov. 25, 2020 (JP) .................... 2020-195034

(51) Int. Cl.
*A61B 8/00* (2006.01)
*B06B 1/02* (2006.01)
(Continued)

(52) U.S. Cl.
CPC .......... *A61B 8/4494* (2013.01); *A61B 8/4444* (2013.01); *A61B 8/54* (2013.01); *B06B 1/0207* (2013.01); *B06B 1/0622* (2013.01); *B06B 1/0681* (2013.01); *G01S 15/8906* (2013.01); *B06B 2201/76* (2013.01)

(58) Field of Classification Search
None
See application file for complete search history.

(56) References Cited

U.S. PATENT DOCUMENTS

| 2004/0085858 A1 | 5/2004 | Khuri-Yakub et al. |
| 2011/0198966 A1 | 8/2011 | Fujii et al. |
| (Continued) | | |

FOREIGN PATENT DOCUMENTS

| JP | 2011-167021 A | 8/2011 |
| JP | 2015-188208 A | 10/2015 |
| (Continued) | | |

*Primary Examiner* — Colin T. Sakamoto
*Assistant Examiner* — Tommy T Ly
(74) *Attorney, Agent, or Firm* — Harness, Dickey & Pierce, P.L.C.

(57) ABSTRACT

A piezoelectric actuator includes a vibrating plate including a first surface that closes an opening provided in a substrate and a second surface in which a plurality of piezoelectric elements is provided, a suppression part configured to suppress a vibration of the vibrating plate, and a first wall and a second wall protruding from the first surface to the opening. When a portion where the first electrode, the piezoelectric layer and the second electrode overlap each other is an active part of the piezoelectric element, the first wall and the second wall are provided to sandwich the active part in plan view from the stacking direction of the first electrode, the piezoelectric layer and the second electrode, and the second wall is different from the first wall at least in one of the width, height, length and physical property.

10 Claims, 24 Drawing Sheets

(51) Int. Cl.
*B06B 1/06* (2006.01)
*G01S 15/89* (2006.01)

(56) References Cited

U.S. PATENT DOCUMENTS

| | | | |
|---|---|---|---|
| 2015/0141827 A1* | 5/2015 | Kiyose | A61B 8/4483 29/25.35 |
| 2015/0258573 A1* | 9/2015 | Kojima | B06B 1/0622 310/327 |
| 2017/0227502 A1 | 8/2017 | Kojima et al. | |
| 2018/0192995 A1* | 7/2018 | Osawa | A61B 8/4494 |
| 2020/0130014 A1 | 4/2020 | Suzuki et al. | |

FOREIGN PATENT DOCUMENTS

| | | | |
|---|---|---|---|
| JP | 2017-139651 A | | 8/2017 |
| JP | 2018133622 A | * | 8/2018 |
| JP | 2020-068453 A | | 4/2020 |
| JP | 2020-068455 A | | 4/2020 |
| WO | 2004-016036 A2 | | 2/2004 |

* cited by examiner

PIEZOELECTRIC ACTUATOR, ULTRASOUND ELEMENT, ULTRASOUND PROBE, ULTRASOUND DEVICE, AND ELECTRONIC DEVICE

The present application is based on, and claims priority from JP Application Serial Number 2020-195034, filed Nov. 25, 2020, the disclosure of which is hereby incorporated by reference herein in its entirety.

BACKGROUND

1. Technical Field

The present disclosure relates to a piezoelectric actuator, an ultrasound element, an ultrasound probe, an ultrasound device, and an electronic device.

2. Related Art

In the related art, as disclosed in JP-A 2015-188208, an ultrasound sensor is known in which a substrate in which opening is formed, a vibrating plate provided at the substrate to seal the opening, and a plurality of piezoelectric elements including a first electrode, a piezoelectric layer and a second electrode stacked at the vibrating plate on the side opposite to the opening are provided, and, when a portion where the first electrode, the piezoelectric layer and the second electrode are completely overlap each other in the direction in which the first electrode, the piezoelectric layer and the second electrode are stacked is an active part, a suppression part that suppresses the vibration of the vibrating plate and a partition wall that surrounds the opening are provided between active parts adjacent to each other.

In the above-mentioned configuration, the partitions wall that surround the opening have the same shape and physical property. As such, when the vibration of the vibrating plate is transmitted to the partition walls, the partition walls tend to resonate, and a vibration of unnecessary frequencies due to the resonance of the partition walls is generated.

SUMMARY

A piezoelectric actuator includes a substrate in which an opening is formed, a vibrating plate provided at the substrate such that a first surface of the vibrating plate closes the opening, a piezoelectric element provided corresponding to the opening at a second surface of the vibrating plate on a side opposite to the first surface, a suppression part configured to suppress a vibration of the vibrating plate, a first wall protruding from the first surface to the opening, and a second wall protruding to the opening from a position different from a position of the first wall at the first surface. In the piezoelectric element, a first electrode, a piezoelectric layer and a second electrode are stacked in this order from the second surface side, when a portion where the first electrode, the piezoelectric layer and the second electrode overlap each other is an active part, the first wall and the second wall are provided to sandwich the active part in plan view from a stacking direction, and the second wall is different from the first wall at least in one of a width, a height, a length and a physical property.

An ultrasound element includes the above-described piezoelectric actuator, a transmission circuit configured to cause the piezoelectric actuator to transmit ultrasound waves, and a reception circuit configured to cause the piezoelectric actuator to receive ultrasound waves.

An ultrasound probe includes the above-described ultrasound element, and a housing configured to house the ultrasound element.

An ultrasound device includes the ultrasound element, and a controller configured to control the ultrasound element.

An electronic device includes the above-described piezoelectric actuator.

DESCRIPTION OF EXEMPLARY EMBODIMENTS

1. Embodiment 1

An ultrasound measurement device 1 according to an embodiment 1 is described below with reference to FIG. 1 and FIG. 2.

Figure 1:
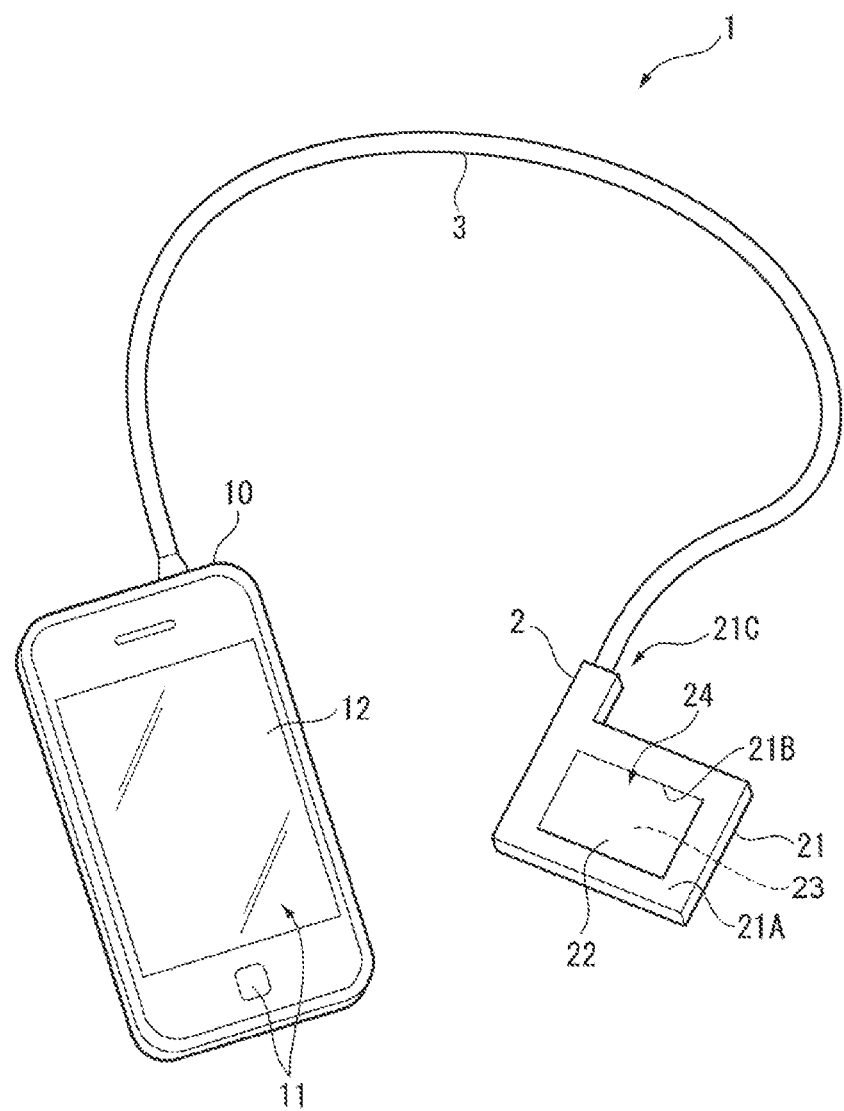
FIG. 1 is a perspective view illustrating a schematic configuration of an ultrasound measurement device according to an embodiment 1.
Figure 2:
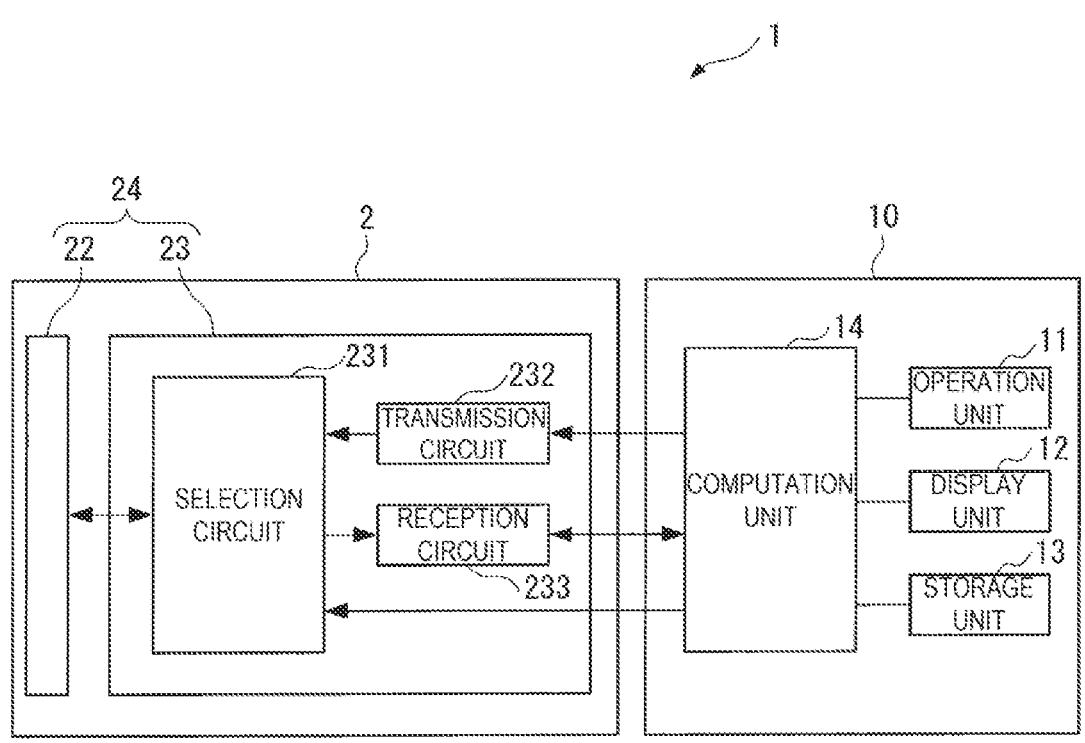
FIG. 2 is a block diagram illustrating a schematic configuration of the ultrasound measurement device according to the embodiment 1.

As illustrated in FIG. 1 and FIG. 2, the ultrasound measurement device 1 as an ultrasound device and an electronic device of this embodiment includes an ultrasound probe 2, and a controller 10 electrically coupled to the ultrasound probe 2 through a cable 3.

By attaching the ultrasound probe 2 to a biological surface of a human body or the like, outputting ultrasound waves from the ultrasound probe 2, and receiving ultrasound waves reflected inside a living body at the ultrasound probe 2, the ultrasound measurement device 1 can acquire an inner tomographic image inside the living body and measure the state of organs inside the living body such as blood flow on the basis of the received signal.

The ultrasound probe 2 includes an ultrasound element 24, and a housing 21 that houses the ultrasound element 24.

The ultrasound element 24 includes a piezoelectric actuator 22, and a circuit board 23 that controls the piezoelectric actuator 22.

The circuit board 23 includes a transmission circuit 232 for transmitting ultrasound waves from the piezoelectric actuator 22, a reception circuit 233 for receiving ultrasound waves at the piezoelectric actuator 22 and outputting a reception signal, and a selection circuit 231.

Under the control of the controller 10, the selection circuit 231 switches between a transmission coupling for coupling the piezoelectric actuator 22 and the transmission circuit 232, and a reception coupling for coupling the piezoelectric actuator 22 and the reception circuit 233.

When switched to the transmission coupling, the transmission circuit 232 outputs a transmission signal for causing the piezoelectric actuator 22 to transmit ultrasound waves through the selection circuit 231.

When switched to the reception coupling, the reception circuit 233 outputs, to the controller 10, the reception signal input from the piezoelectric actuator 22 through the selection circuit 231. After performing signal processing such as conversion of the reception signal into a digital signal, removal of noise components and amplification to a desired signal level, the reception circuit 233 outputs the processed reception signal to the controller 10.

The housing 21 is formed in a rectangular box shape, for example. One surface of the housing 21 is a sensor surface 21A, and the sensor surface 21A is provided with a sensor window 21B. A part of the piezoelectric actuator 22 is exposed from the sensor window 21B. In addition, a passing hole 21C for the cable 3 is provided in a part of the housing 21, and the cable 3 is coupled to the circuit board 23 from the passing hole 21C.

The controller 10 includes an operation unit 11, a display unit 12, a storage unit 13, and a computation unit 14. The controller 10 controls the ultrasound element 24. As the controller 10, for example, a general-purpose terminal apparatus such as a smartphone and a personal computer, or a dedicated terminal apparatus for operating the ultrasound probe 2 may be used.

The operation unit 11 is a user interface for operating the ultrasound measurement device 1, and a touch panel, an operation button and the like provided on the display unit 12 may be used, for example. The display unit 12 is composed of, for example, a liquid crystal display or the like, and displays images. The storage unit 13 stores various programs and various data for controlling the ultrasound measurement device 1. The computation unit 14 is composed of an arithmetic circuit such as a CPU and a storage circuit such as a memory, for example. By reading and executing various programs stored in the storage unit 13, the computation unit 14 controls a process of generating and outputting the transmission signal for the transmission circuit 232, and controls the gain setting and frequency setting of reception signals for the reception circuit 233.

The piezoelectric actuator 22 according to the embodiment 1 is described below with reference to FIG. 3 to FIG. 7 and FIG. 11. As described later, in the piezoelectric actuator 22, a width W1 of a first wall 418 and a width W2 of a second wall 419 are different from each other. Note that FIG. 5 illustrates a state where a sealing plate 42 is detached for convenience of illustration of the inner configuration of the piezoelectric actuator 22. In addition, in the drawing, the dimensional ratio of each component differs from the actual one for convenience of illustration.

In the coordinates indicated in the drawings, the three axes orthogonal to each other are described as the X axis, the Y axis, and the Z axis. The direction along the X axis is the "X direction", the direction along the Y axis is the "Y direction", the direction along the Z axis is the "Z direction", and the arrow direction is the plus direction. In addition, in plan view from the Z direction, the surface on the plus side in the Z direction is described as the top surface, and the surface on the minus side in the Z direction opposite to the plus side is described as the bottom surface.

Figure 3:
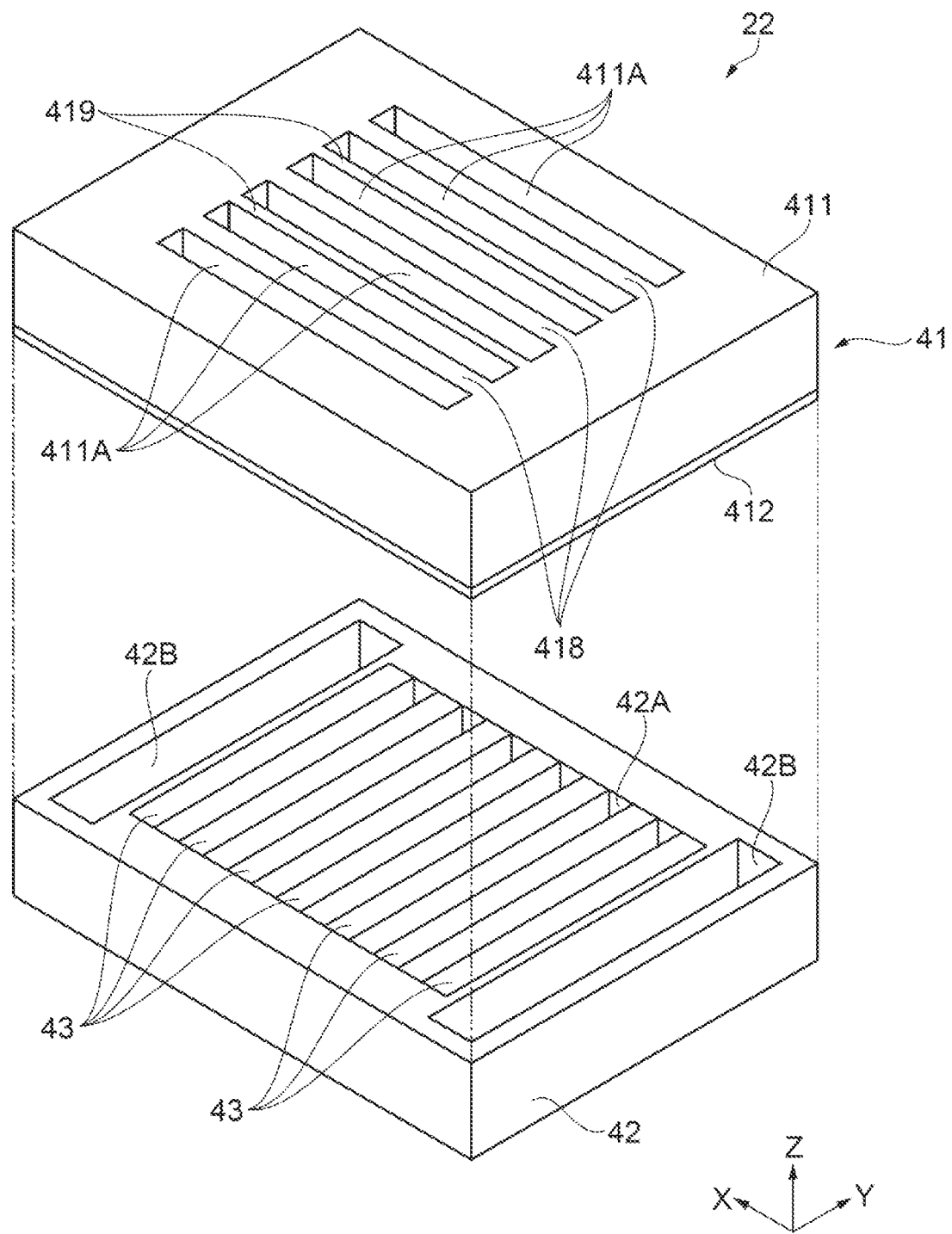
FIG. 3 is a perspective view illustrating a schematic configuration of a piezoelectric actuator according to the embodiment 1.

As illustrated in FIG. 3, the piezoelectric actuator 22 includes a base part 41, the sealing plate 42, and a suppression part 43.

Figure 4:
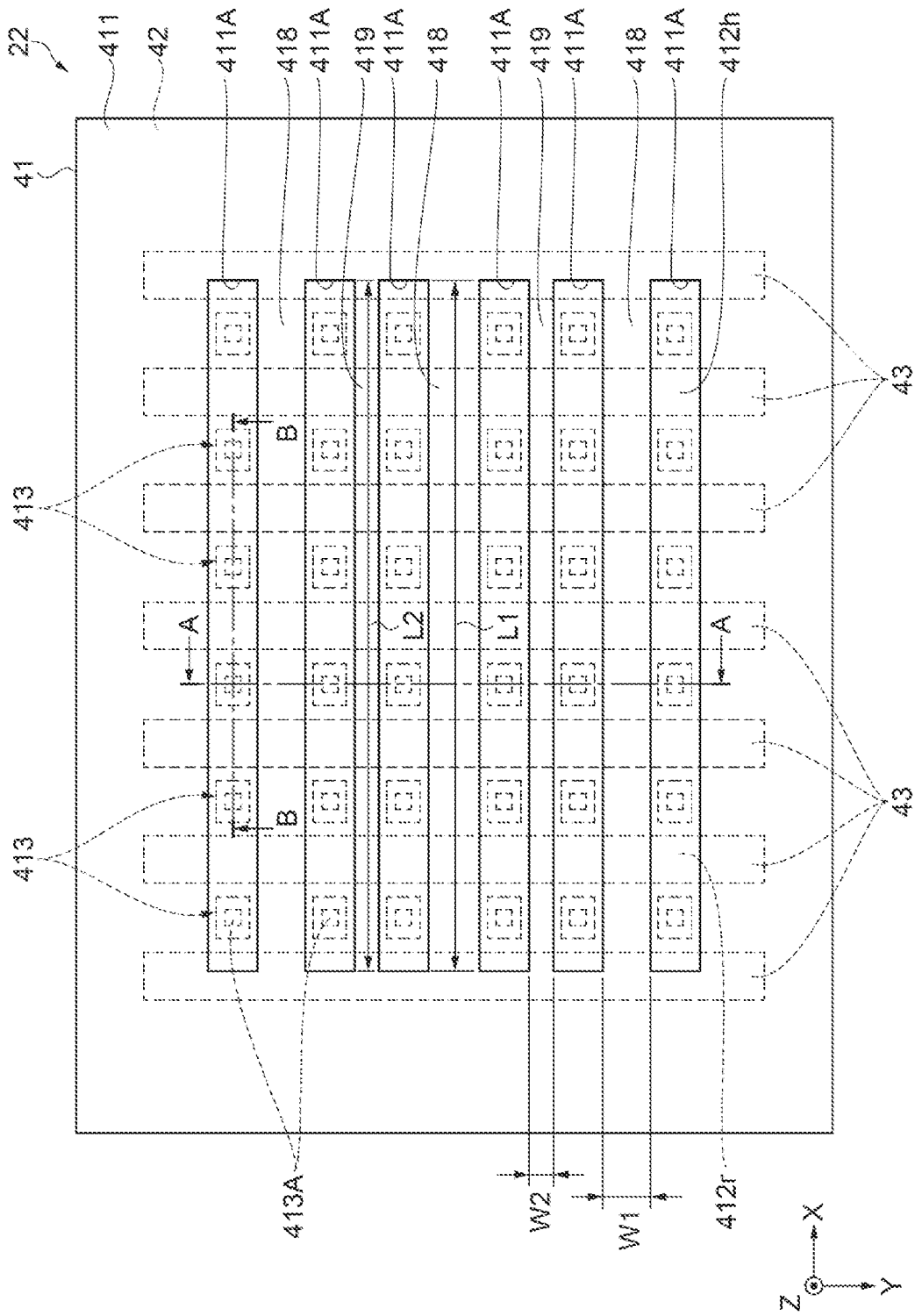
FIG. 4 is a plan view of the piezoelectric actuator according to the embodiment 1 as viewed from a base part side.
Figure 5:
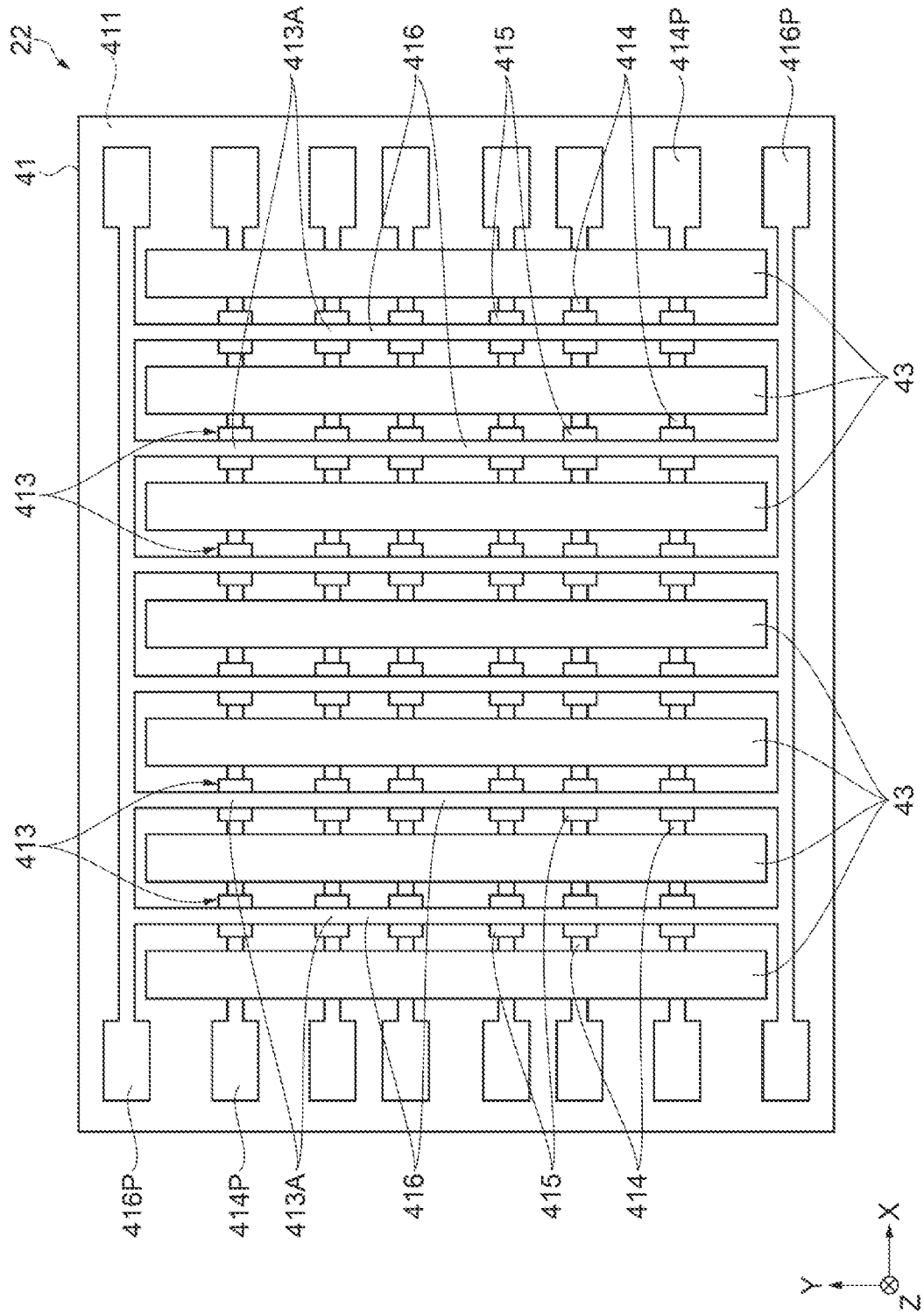
FIG. 5 is a plan view of the piezoelectric actuator according to the embodiment 1 as viewed from a sealing plate side.
Figure 6:
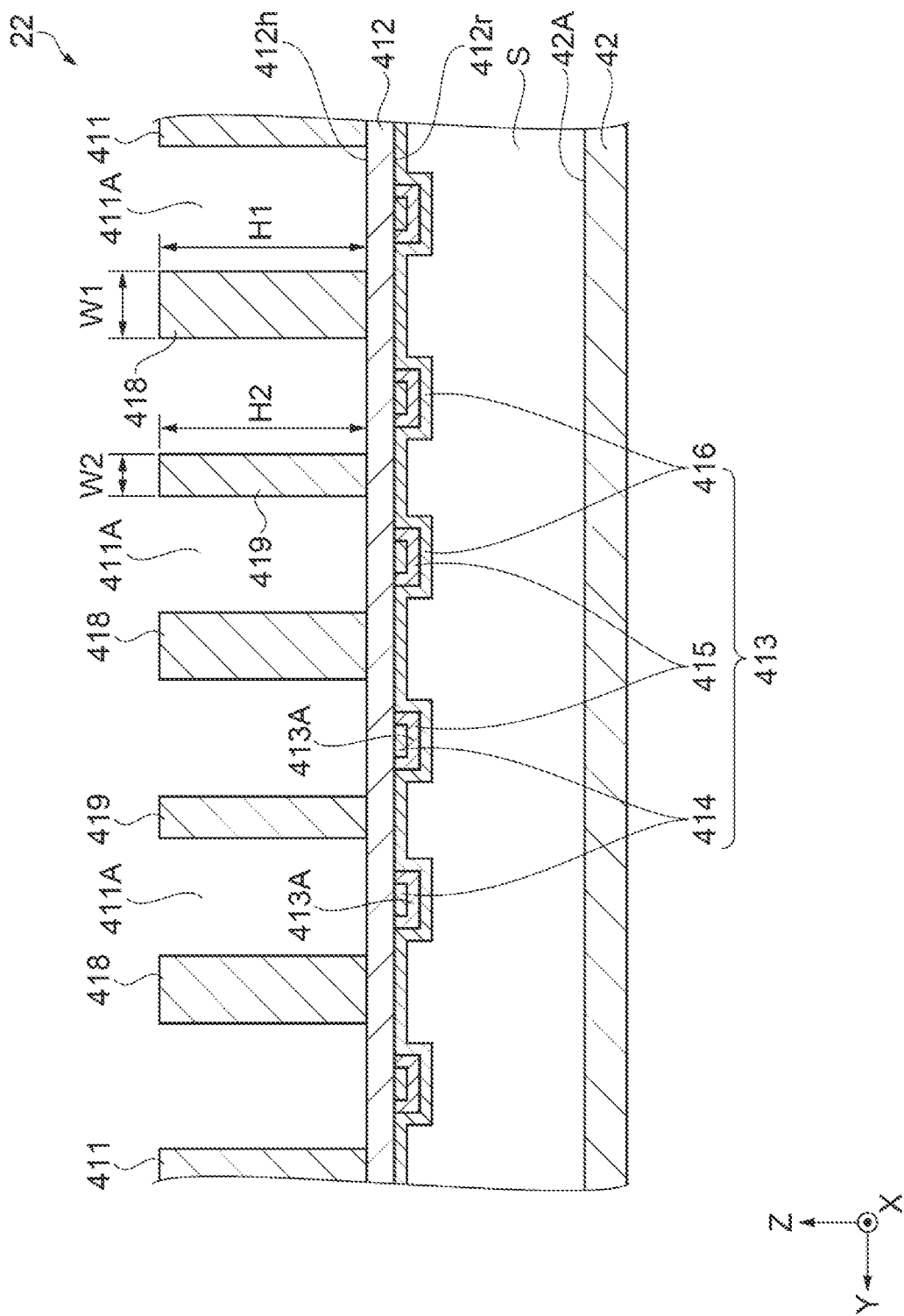
FIG. 6 is a sectional view taken along a line A-A in FIG. 4.

As illustrated in FIG. 3, FIG. 4 and FIG. 6, the base part 41 includes a substrate 411 in which an opening 411A is formed, a vibrating plate 412 that closes the opening 411A, a plurality of piezoelectric elements 413 provided at the vibrating plate 412, the first wall 418 provided at the vibrating plate 412, and the second wall 419 provided at the vibrating plate 412. Note that an acoustic matching layer, an acoustic lens and the like may be provided at the opening 411A of the substrate 411.

The substrate 411 is a semiconductor substrate formed of silicon or the like. In this embodiment, the substrate 411 is formed of silicon. In plan view from the Z direction, the substrate 411 includes the opening 411A at a center portion of the substrate 411.

The vibrating plate 412 is a thin film composed of silicon oxide, a laminate of silicon oxide and zirconium oxide or the like, for example. The vibrating plate 412 includes a first surface 412h, and a second surface 412r on the side opposite to the first surface 412h. The first surface 412h is the top surface of the vibrating plate 412, and the second surface 412r is the bottom surface of the vibrating plate 412. The vibrating plate 412 is provided at the bottom surface of the substrate 411, and the first surface 412h of the vibrating plate 412 closes the opening 411A of the substrate 411 from the bottom surface side of the substrate 411.

As illustrated in FIG. 3, FIG. 4 and FIG. 6, the first wall 418 is provided at the first surface 412h of the vibrating plate 412, and protrudes to the opening 411A from the first surface 412h. In this embodiment, in plan view from the Z direction, the first wall 418 extends in parallel with the X direction. In addition, the end portions of the first wall 418 on the plus side in the X direction and the minus side in the X direction are coupled with peripheries of the opening 411A on the plus side in the X direction and the minus side in the X direction, respectively.

The second wall 419 is provided at the first surface 412h of the vibrating plate 412, and protrudes to the opening 411A from a position different from that of the first wall 418 in the first surface 412h. In this embodiment, in plan view from the Z direction, the second wall 419 extends in parallel with the X direction, and the first wall 418 and the second wall 419 are disposed at adjacent positions side by side in the Y direction. In addition, the end portions of the second wall 419 on the plus side in the X direction and the minus side in the X direction are coupled with the peripheries of the opening 411A on the plus side in the X direction and the minus side in the X direction, respectively.

In this embodiment, in plan view from the Z direction, the first wall 418 and the second wall 419 are alternately disposed side by side in the Y direction, and function as partition walls that partition the opening 411A.

Note that in this embodiment, the first wall 418 and the second wall 419 are formed by patterning the substrate 411 by a photolithography technique. In this manner, the first wall 418 and the second wall 419 can be formed using the same material as that of the substrate 411. For example, by using a silicon substrate as the substrate 411, the first wall 418 and the second wall 419 can be formed using silicon. In this manner, by using the same material for the material of the first wall 418 and the material of the second wall 419, the physical property of the first wall 418 and the physical property of the second wall 419 can be made substantially equal to each other.

Here, in plan view from the Z direction, the distance from the edge of the first wall 418 on the plus side in the Y direction to the edge on the minus side in the Y direction is the width W1 of the first wall 418, and the distance from the end portion of the first wall 418 on the plus side in the X direction and the end portion on the minus side in the X direction is a length L1 of the first wall 418. In addition, in plan view from the X direction, the distance from the first surface 412h of the vibrating plate 412 corresponding to the bottom surface of the first wall 418 to the top surface of the first wall 418 is a height H1 of the first wall 418.

Likewise, in plan view from the Z direction, the distance from the edge of the second wall 419 on the plus side in the Y direction to the edge on the minus side in the Y direction is the width W2 of the second wall 419, and the distance from the end portion of the second wall 419 on the plus side in the X direction to the end portion on the minus side in the X direction is a length L2 of the second wall 419. In addition, in plan view from the X direction, the distance from the first surface 412h of the vibrating plate 412 corresponding to the bottom surface of the second wall 419 to the top surface of the second wall 419 is a height H2 of the second wall 419.

In this embodiment, the width W1 of the first wall 418 and the width W2 of the second wall 419 are different from each other. More specifically, the width W1 of the first wall 418 is greater than the width W2 of the second wall 419. The length L1 of the first wall 418 and the length L2 of the second wall 419 are substantially equal to each other. The height H1 of the first wall 418 and the height H2 of the second wall 419 are substantially equal to each other. Note that "substantially" means that manufacturing errors, dimensional tolerances and the like are included.

In this manner, the width W2 of the second wall 419 is different from the width W1 of the first wall 418, and thus the first wall 418 and the second wall 419 have vibration characteristics different from each other. More specifically, since the first wall 418 and the second wall 419 have resonance frequencies different from each other, the vibrations of the first wall 418 and the second wall 419 are less coupled, and the intensity of the resonance of each of the first wall 418 and the second wall 419 is small when the vibration of the vibrating plate 412 is transmitted to the first wall 418 and the second wall 419.

Figure 7:
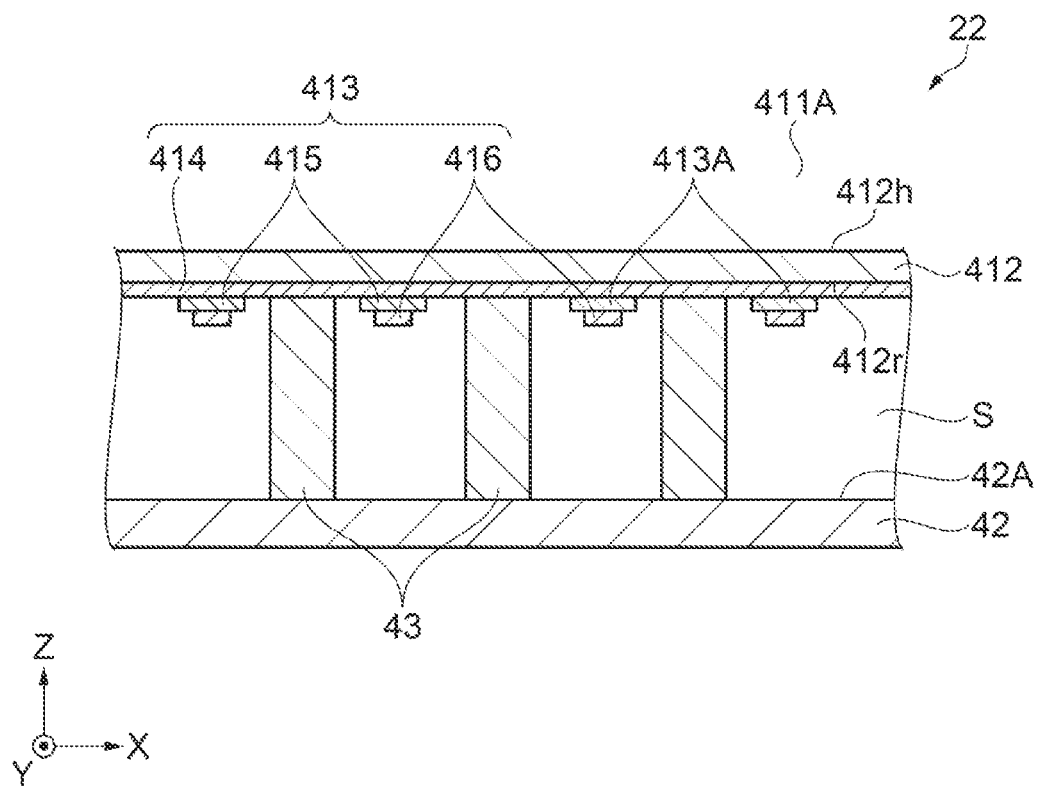
FIG. 7 is a sectional view taken along a line B-B in FIG. 4.

As illustrated in FIG. 4, FIG. 6 and FIG. 7, the piezoelectric element 413 is provided at the second surface 412r of the vibrating plate 412 on the side opposite to the first surface 412h at a position corresponding to the opening 411A of the substrate 411. More specifically, in plan view from the Z direction, the piezoelectric element 413 is disposed to overlap the opening 411A. In addition, the piezoelectric element 413 is disposed in a sandwiched manner between the first wall 418 and the second wall 419 functioning as partition walls that partition the opening 411A.

As illustrated in FIG. 5 to FIG. 7, the piezoelectric element 413 is a laminate in which a first electrode 414, a piezoelectric layer 415 and a second electrode 416 are stacked. The first electrode 414, the piezoelectric layer 415 and the second electrode 416 are stacked in the order of the first electrode 414, the piezoelectric layer 415 and the second electrode 416 from the second surface 412r side of the vibrating plate 412. In plan view from the Z direction, which is the stacking direction in which the first electrode 414, the piezoelectric layer 415 and the second electrode 416 are stacked, the portion where the first electrode 414, the piezoelectric layer 415 and the second electrode 416 overlap each other functions as an active part 413A.

The first electrode 414, which extends in the X direction, is continuously provided across a plurality of the active parts 413A. End portions on the plus side in the X direction and the minus side in the X direction of a plurality of the first electrodes 414 arranged in the Y direction are electrically coupled with first electrode terminals 414P provided at the outer peripheral edges on the plus side in the Y direction and the minus side in the Y direction of the substrate 411.

In plan view from the Z direction, the piezoelectric layer 415 is disposed in a matrix corresponding to an intersection of the first electrode 414 and the second electrode 416. Typically, a composite oxide with a perovskite structure based on lead zirconate titanate may be used for the piezoelectric layer 415. In this manner, the amount of displacement of the piezoelectric element 413 can be easily ensured. In addition, a composite oxide with a perovskite structure that does not contain lead may be used for the piezoelectric layer 415. In this manner, the piezoelectric actuator 22 can be achieved using non-lead materials that have less impact on the environment.

The second electrode 416, which extends in the Y direction, is continuously provided across a plurality of the active parts 413A. The end portions of a plurality of the second electrodes 416 arranged in the X direction on the plus side in the Y direction and the minus side in the Y direction are drawn to the outer peripheral edges on the plus side in the X direction and the minus side in the X direction of the substrate 411. The end portion of the second electrode 416 drawn to the outer peripheral edges of the substrate 411 is wired and electrically coupled with a second electrode terminal 416P provided at the outer peripheral edges on the plus side in the X direction and the minus side in the X direction of the substrate 411.

The material of the first electrode 414 and the second electrode 416 is not limited as long as the material has conductivity. As an example of the material of the first electrode 414 and the second electrode 416, a conductive layer of iridium, platinum, titanium and the like may be used, for example. Note that the conductive layer may be a single layer or multiple layers.

The plurality of piezoelectric elements 413 is disposed in a matrix along the X direction along the X axis, which is a first axis orthogonal to the Z direction as the stacking direction in which the first electrode 414, the piezoelectric layer 415 and the second electrode 416 are stacked at the active part 413A, and the Y direction along the Y axis, which is a second axis orthogonal to the X axis as the first axis. In this embodiment, a single transmission-reception line is formed by the plurality of piezoelectric elements 413 disposed side by side in a line in the X direction, and a matrix of the plurality of piezoelectric elements 413 is formed by a plurality of the transmission-reception lines disposed side by side in the Y direction.

As illustrated in FIG. 4, FIG. 5 and FIG. 7, the suppression part 43 is provided at the second surface 412r of the vibrating plate 412. The top surface of the suppression part 43 is joined to the second surface 412r of the vibrating plate 412, and the bottom surface of the suppression part 43 is joined to the sealing plate 42. In this manner, the suppression part 43 can fix the vibrating plate 412 and suppress the vibration of the vibrating plate 412.

The suppression part 43 is provided corresponding to the active part 413A. More specifically, as illustrated in FIG. 4 and FIG. 5, in plan view from the Z direction, the suppression part 43 is extended in parallel with the Y direction, and a plurality of the suppression parts 43 is disposed side by side in the X direction. Further, the plurality of piezoelectric elements 413 disposed side by side in the Y direction is disposed between the plurality of suppression parts 43. In other words, in plan view from the Z direction, which is the stacking direction in which the first electrode 414, the piezoelectric layer 415 and the second electrode 416 are stacked in the active part 413A, the suppression parts 43 are provided to sandwich the active part 413A in the X direction.

In addition, as illustrated in FIG. 4 and FIG. 6, in plan view from the Z direction, which is the stacking direction in which the first electrode 414, the piezoelectric layer 415 and the second electrode 416 are stacked in the active part 413A, the first wall 418 and the second wall 419 are provided to sandwich the active part 413A in the Y direction.

That is, the suppression part 43 is disposed at the vibrating plate 412 on the plus side in the X direction and the minus side in the X direction of the active part 413A, and the first wall 418 and the second wall 419 are disposed at the vibrating plate 412 on the plus side in the Y direction and the minus side in the Y direction of the active part 413A. In this manner, the vibration range of the vibrating plate 412 in the X direction and the Y direction can be limited with the suppression part 43, the first wall 418 and the second wall 419.

For example, the suppression part 43 is composed of a resin material, and can be formed by applying a photosensitive resin material to the vibrating plate 412 by spin coating, sputtering or the like, and then patterning it by photolithography techniques.

Note that while the suppression part 43 is provided at the second surface 412r of the vibrating plate 412 in this embodiment as described above, the suppression part 43 may be provided at the first surface 412h of the vibrating plate 412. It should be noted that the vibration of the vibrating plate 412 can be more readily suppressed when the suppression part 43 is provided at the second surface 412r of the vibrating plate 412.

As illustrated in FIG. 3, FIG. 6 and FIG. 7, in plan view from the Z direction, the sealing plate 42 is formed in substantially the same shape as the substrate 411. The sealing plate 42 is disposed opposite to the second surface 412r of the vibrating plate 412. The top surface of the sealing plate 42 and the bottom surface of the substrate 411 are joined to each other through the vibrating plate 412. In plan view from the Z direction, the sealing plate 42 includes a recess 42A that is depressed downward at a center portion of the top surface. The piezoelectric element 413 provided at the second surface 412r of the vibrating plate 412 is sealed in space S formed in the recess 42A.

As illustrated in FIG. 3 and FIG. 5, the sealing plate 42 includes a through hole 42B at a position corresponding to the first electrode terminal 414P and the second electrode terminal 416P. In the through hole 42B, for example, a wiring member such as a flexible printed circuit (FPC) not illustrated in the drawing is inserted. Through the wiring member not illustrated in the drawing, the first electrode terminal 414P and the second electrode terminal 416P, and the circuit board 23 are electrically coupled with each other.

In transmission of ultrasound waves, a drive signal is input to the first electrode terminal 414P and a common bias signal is input to the second electrode terminal 416P from the circuit board 23 through the wiring member not illustrated in the drawing. By controlling the signal intensity and signal input timing of the drive signal input to the first electrode terminal 414P, a potential difference is caused between the first electrode 414 and the second electrode 416 of the active part 413A such that the piezoelectric layer 415 vibrates and accordingly the vibrating plate 412 vibrates, thus generating ultrasound waves.

In reception of ultrasound waves, a common bias signal is input from the circuit board 23 to the second electrode terminal 416P. Then, when ultrasound waves from an object is input to the piezoelectric actuator 22 and the vibrating plate 412 is vibrated, the piezoelectric element 413 is deflected and a potential difference is caused between the first electrode 414 and the second electrode 416 in accordance with the deflection of the piezoelectric element 413. In this manner, a detection signal corresponding to ultrasound waves from an object is output from the first electrode terminal 414P to the circuit board 23.

Here, influences of the width W1 of the first wall 418 and the width W2 of the second wall 419 on the piezoelectric actuator 22 are described by comparison between this embodiment and a comparative example.

First, the piezoelectric actuator 22a of a comparative example is described with reference to FIG. 8 and FIG. 9.

Figure 8:
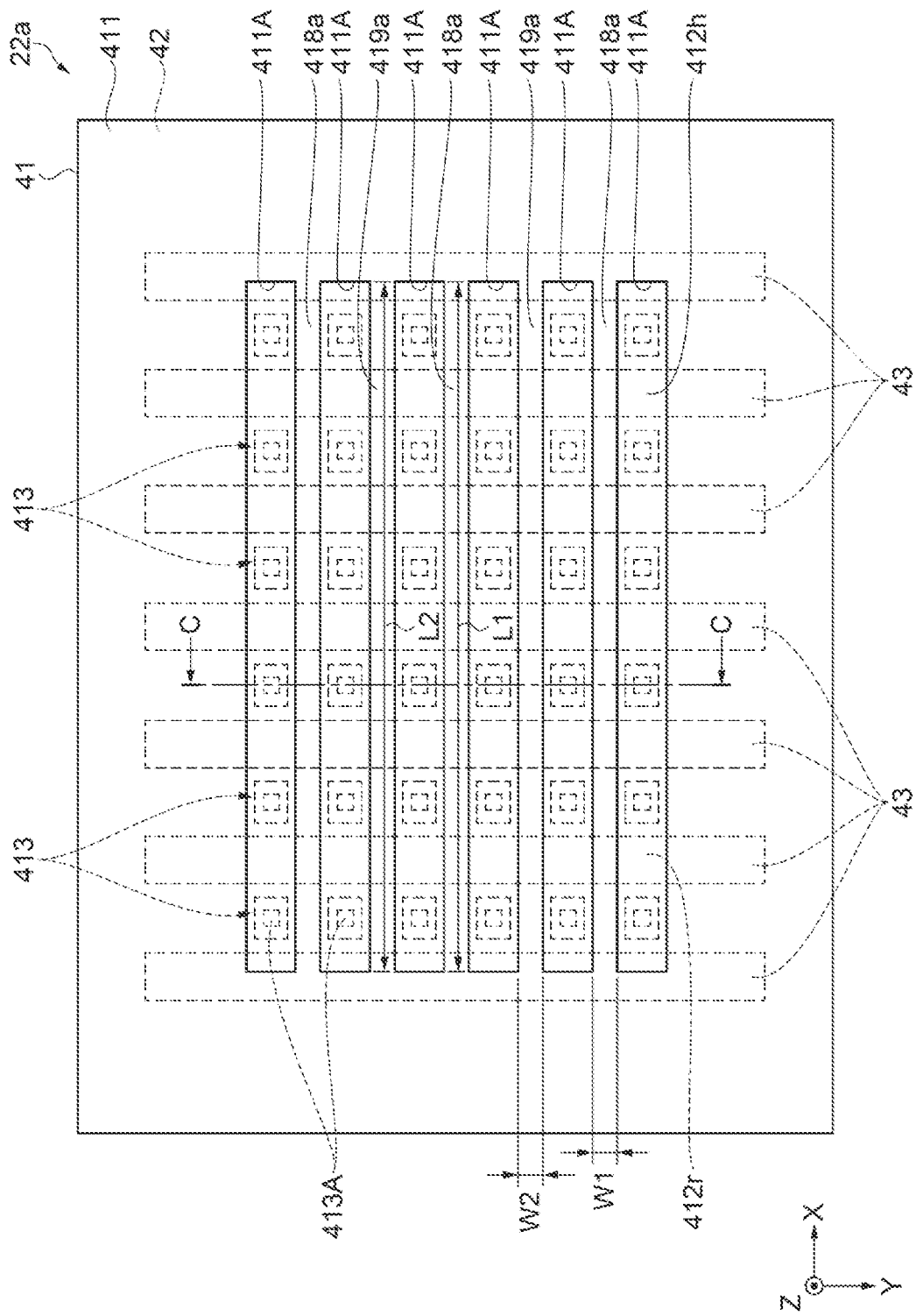
FIG. 8 is a plan view of a piezoelectric actuator according to a comparative example as viewed from a base part side.
Figure 9:
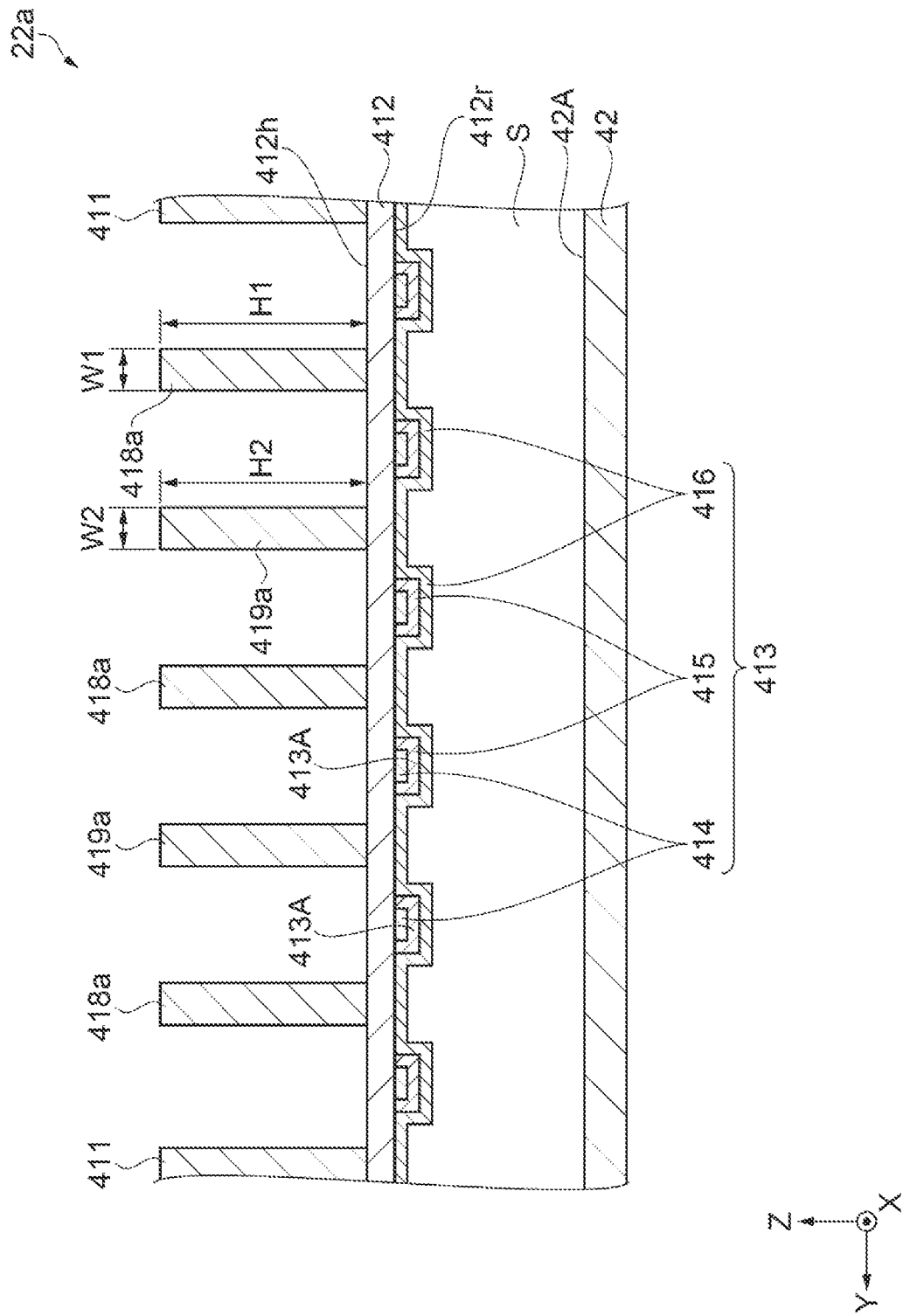
FIG. 9 is a sectional view taken along a line C-C in FIG. 8.

As illustrated in FIG. 8 and FIG. 9, in the piezoelectric actuator 22a of the comparative example, the width W1 of the first wall 418a and the width W2 of the second wall 419a are substantially equal to each other.

Next, frequency spectrums of the piezoelectric actuator 22a of the comparative example and the piezoelectric actuator 22 of this embodiment are described with reference to FIG. 10 and FIG. 11. Note that the frequency spectrum indicates the intensity and type of the frequency of the vibration included in the vibration as a measurement target.

Figure 10:
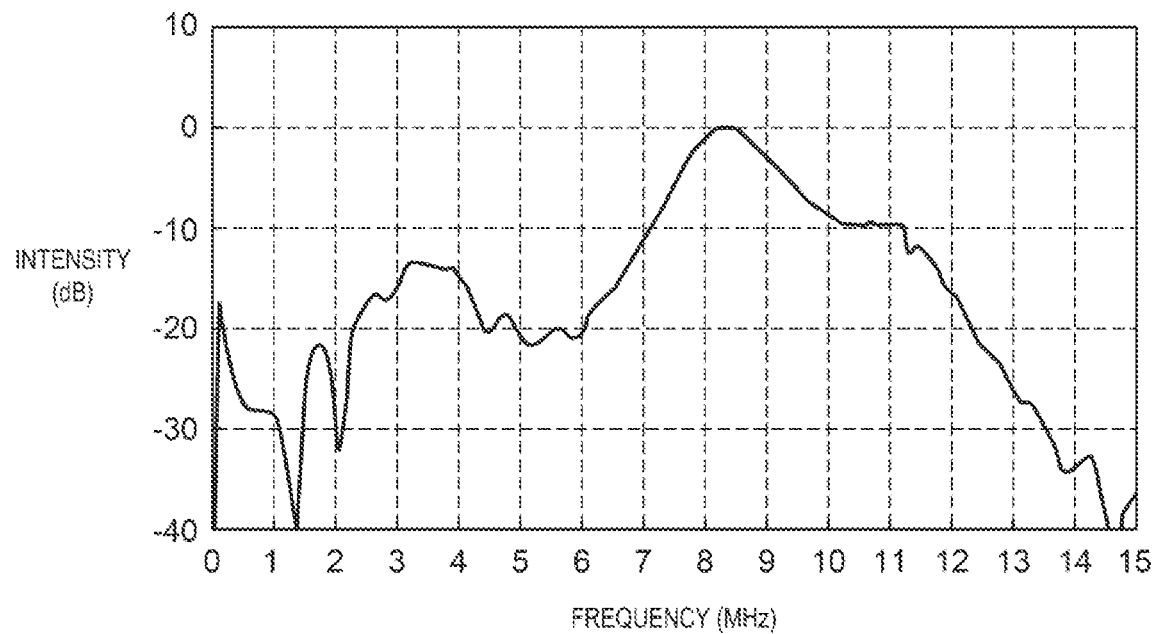
FIG. 10 is a diagram illustrating a frequency spectrum of a piezoelectric actuator according to a comparative example.

As illustrated in FIG. 10, in the frequency spectrum of the piezoelectric actuator 22a of the comparative example, the intensity at 8 to 9 MHz, which are desired frequencies, is high, but the band width is narrow. In addition, the intensity of the vibration of unnecessary frequencies other than the desired frequency, such as 3 to 4 MHz, is also high. The reason for this is that, in the piezoelectric actuator 22a, the width W1 of the first wall 418a and the width W2 of the second wall 419a are substantially equal to each other and thus the first wall 418 and the second wall 419 have substantially the same resonance frequency, and consequently, when the vibration of the vibrating plate 412 is transmitted to the first wall 418 and the second wall 419, the vibrations of the first wall 418 and the second wall 419 are easily coupled with each other, thus resulting a high resonance intensity.

Note that such a vibration of unnecessary frequencies due to the resonance of the first wall 418a and the second wall 419a tends to occur in the case where water or a substance with a Young's modulus of several to several tens of MPa such as a silicone resin is present in the opening 411A, i.e., a region between the first wall 418a and the second wall 419a.

Figure 11:
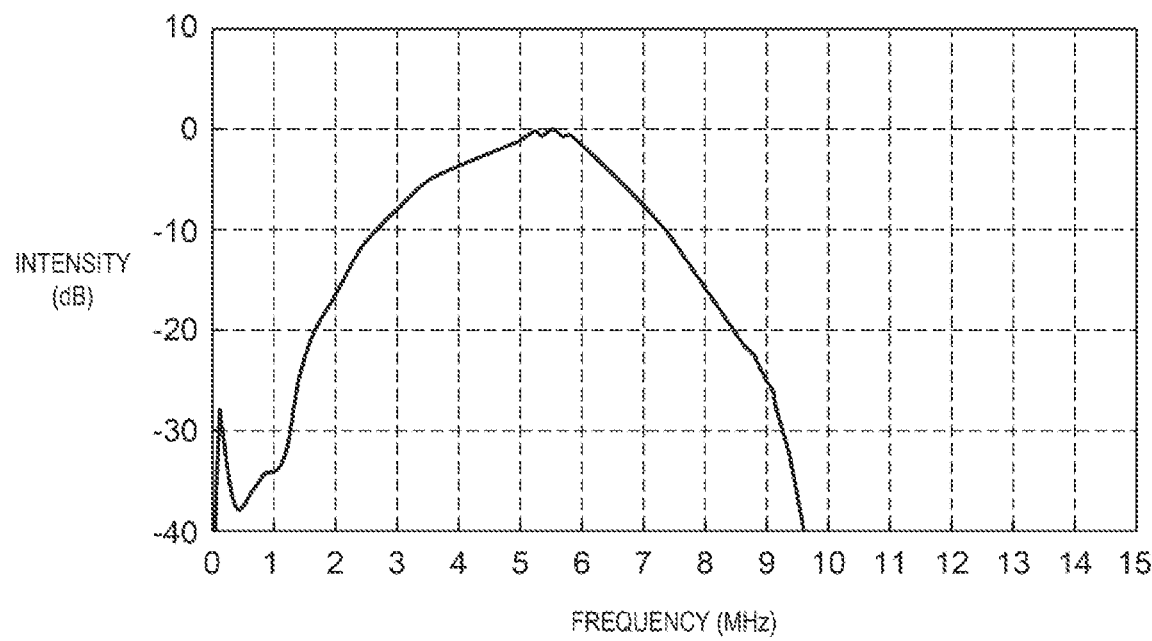
FIG. 11 is a diagram illustrating a frequency spectrum of the piezoelectric actuator according to the embodiment 1.

In contrast, as illustrated in FIG. 11, in the frequency spectrum of the piezoelectric actuator 22 of this embodiment, the intensity at 3 to 7 MHz, which are desired frequencies, is high, and the band width is wide. In addition, the intensity of the vibration at unnecessary frequencies other than the desired frequency is low.

As described above, in this embodiment, since the width W1 of the first wall 418 and the width W2 of the second wall 419 are different from each other, the first wall 418 and the second wall 419 have resonance frequencies different from each other, and thus, when the vibration of the vibrating plate 412 is transmitted to the first wall 418 and the second wall 419, the vibrations of the first wall 418 and the second wall 419 are less coupled, and, the intensity of the resonance of each of the first wall 418 and the second wall 419 is small. As a result, the generation of the vibration of unnecessary frequencies due to the resonance of the first wall 418 and the second wall 419 can be suppressed.

In this manner, according to this embodiment, the following effects can be achieved.

The piezoelectric actuator 22 includes the substrate 411 in which the opening 411A is formed, the vibrating plate 412 including the first surface 412h that closes the opening 411A and the second surface 412r where the plurality of piezoelectric elements 413 are provided, the suppression part 43 that suppresses the vibration of the vibrating plate 412, the first wall 418 protruding from the first surface 412h to the opening 411A, and the second wall 419 protruding to the opening 411A from a position different from a position of the first wall 418 in the first surface 412h. Further, the first wall 418 and the second wall 419 are provided to sandwich the active part 413A in plan view from the Z direction, which is the stacking direction of the first electrode 414, the piezoelectric layer 415 and the second electrode 416, when the active part 413A of the piezoelectric element 413 is the portion where the first electrode 414, the piezoelectric layer 415 and the second electrode 416 overlap each other. Since the width W2 of the second wall 419 is different from the width W1 of the first wall 418, the first wall 418 and the second wall 419 have resonance frequencies different from each other, and thus the generation of the vibration of unnecessary frequencies can be suppressed. In this manner, the piezoelectric actuator 22 with high accuracy can be achieved.

In addition, even in the case where water, a silicone resin or the like is interposed between the first wall 418 and the second wall 419, the generation of the vibration of unnecessary frequencies due to the resonance of the first wall 418 and the second wall 419 can be suppressed.

In addition, even in the case where the vibration of the vibrating plate 412 is transmitted to the first wall 418 and the second wall 419 and the first wall 418 and the second wall 419 are vibrated, the piezoelectric element 413 surrounded by the suppression part 43, the first wall 418 and the second wall 419 can be handled as an independent transducer, and thus the piezoelectric actuator 22 with uniform frequency characteristics can be achieved.

In addition, since leakage of the vibration energy of the vibrating plate 412 can be suppressed through the first wall 418 and the second wall 419, the Q value of the piezoelectric element 413 can be increased, and the piezoelectric actuator 22 with excellent stability of vibration can be achieved.

2. Embodiment 2

Next, a piezoelectric actuator 22b according to an embodiment 2 is described with reference to FIG. 12 and FIG. 13. Note that in the following description, differences from the above-described embodiment 1 are mainly described, the same configurations as those of the embodiment 1 are denoted with the same reference numerals, and overlapping descriptions are omitted.

Figure 13:
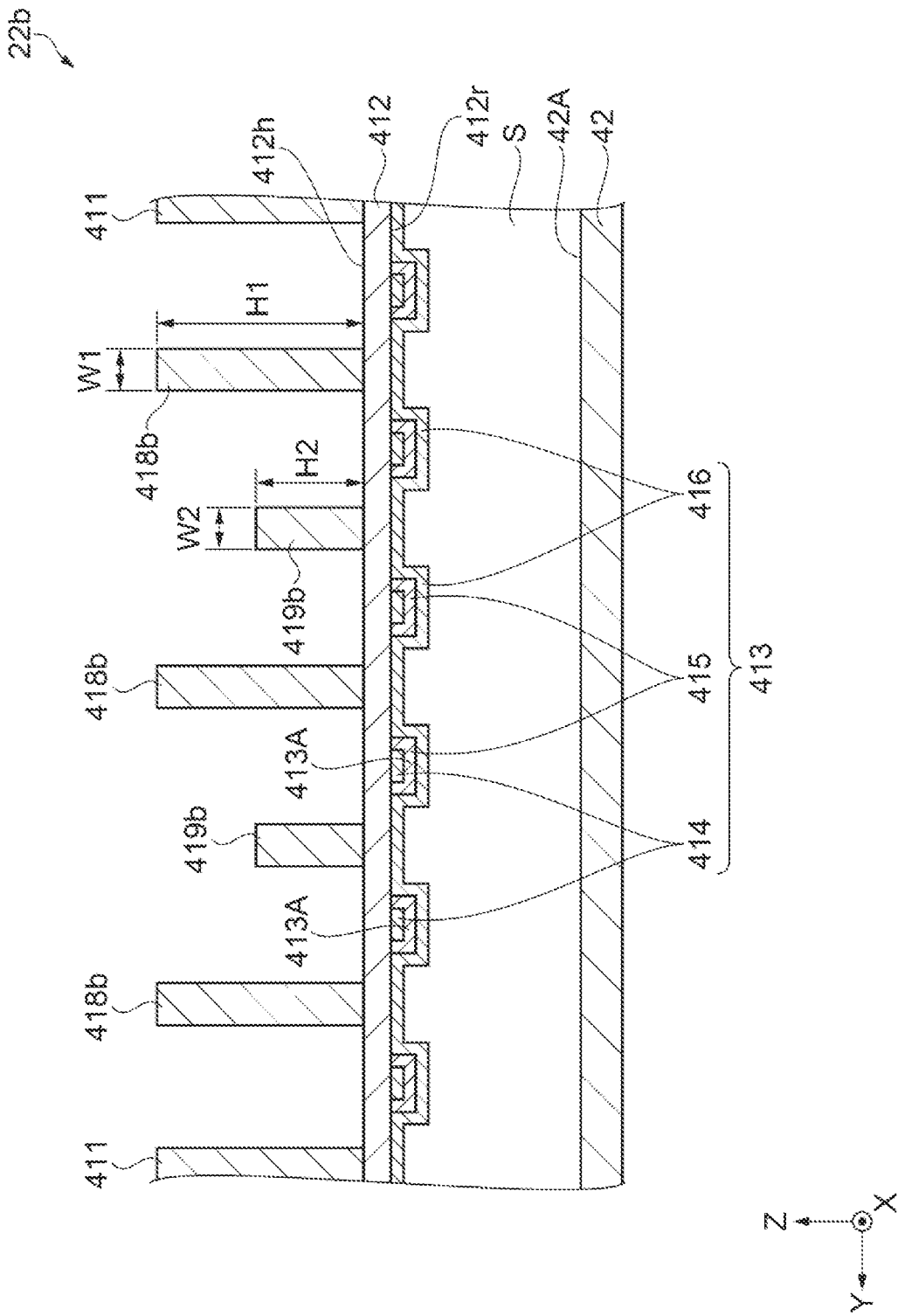
FIG. 13 is a sectional view taken along a line E-E in FIG. 12.

As illustrated in FIG. 13, in the piezoelectric actuator 22b according to this embodiment, the height H1 of a first wall 418b and the height H2 of a second wall 419b are different from each other. More specifically, the height H1 of the first wall 418b is greater than the height H2 of the second wall 419b.

Figure 12:
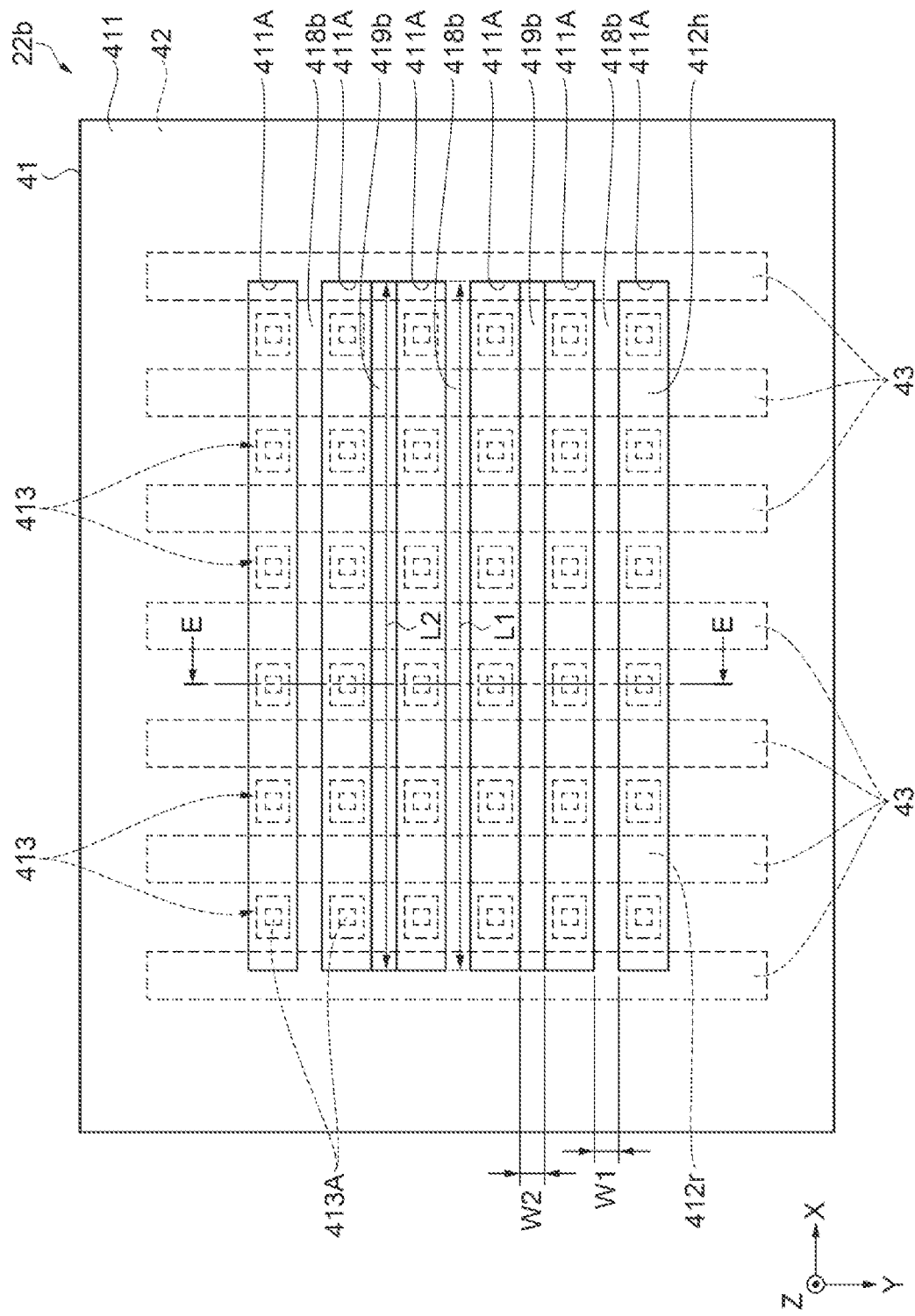
FIG. 12 is a plan view of a piezoelectric actuator according to an embodiment 2 as viewed from a base part side.

As illustrated in FIG. 12 and FIG. 13, in the piezoelectric actuator 22b, the width W1 of the first wall 418b and the width W2 of the second wall 419b are substantially equal to each other. In addition, the length L1 of the first wall 418b and the length L2 of the second wall 419b are substantially equal to each other. In addition, the physical property of the first wall 418b and the physical property of the second wall 419b are substantially equal to each other.

According to this embodiment, effects similar to those of the embodiment 1 can be achieved. Since the height H2 of the second wall 419b is different from the height H1 of the first wall 418b, the first wall 418b and the second wall 419b have resonance frequencies different from each other. As a result, when the vibration of the vibrating plate 412 is transmitted to the first wall 418b and the second wall 419b, the intensity of the resonance of each of the first wall 418b and the second wall 419b is small, and the generation of the vibration of unnecessary frequencies due to the resonance of the first wall 418b and the second wall 419b can be suppressed.

3. Embodiment 3

Next, a piezoelectric actuator 22c according to an embodiment 3 is described with reference to FIG. 14. Note that in the following description, differences from the above-described embodiment 1 are mainly described, the same configurations as those of the embodiment 1 are denoted with the same reference numerals, and overlapping descriptions are omitted.

Figure 14:
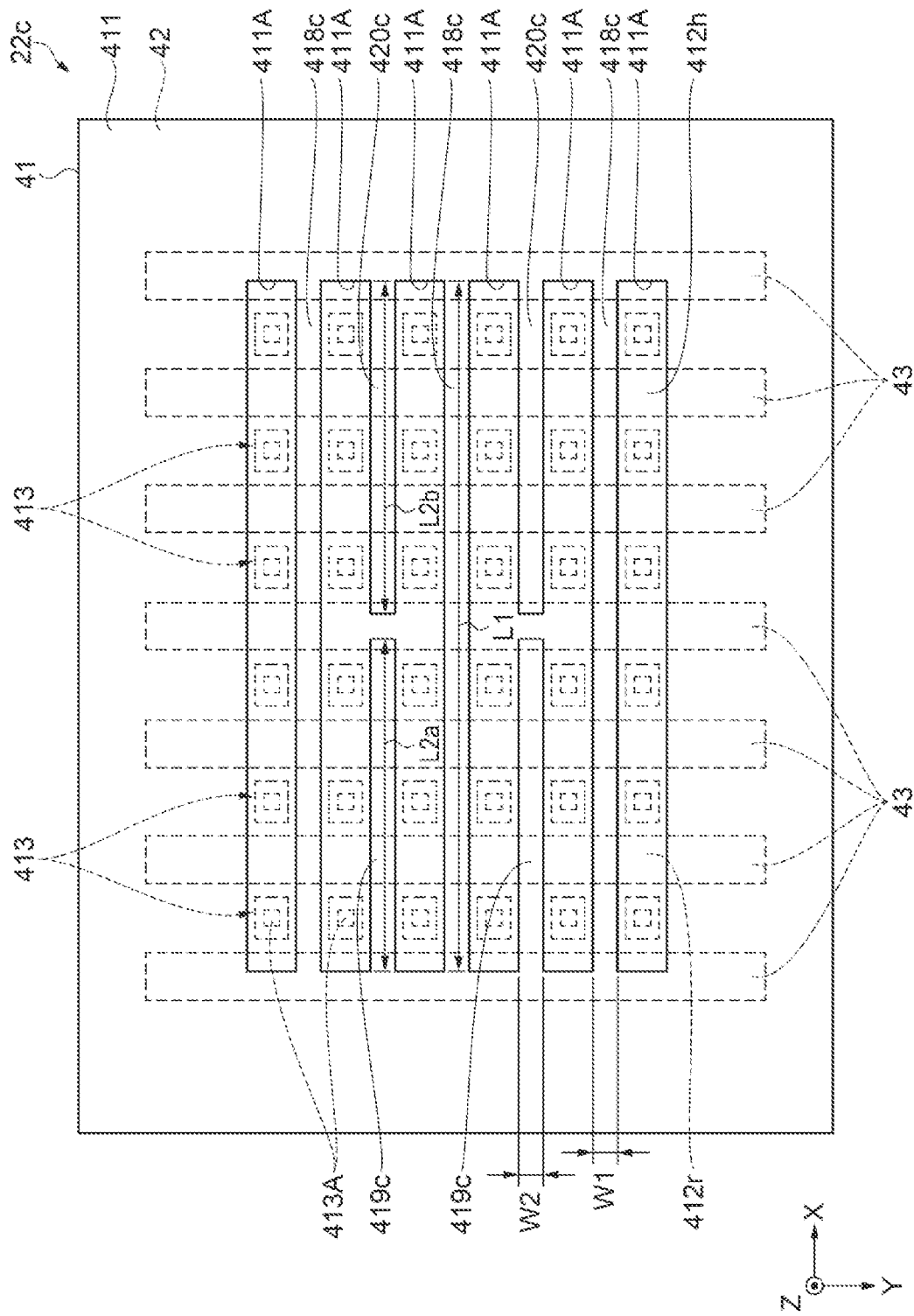
FIG. 14 is a plan view of a piezoelectric actuator according to an embodiment 3 as viewed from a base part side.

As illustrated in FIG. 14, in the piezoelectric actuator 22c according to this embodiment, the length L1 of a first wall 418c and lengths L2a and L2b of second walls 419c and 420c are different from each other. More specifically, the length L1 of the first wall 418c is greater than the lengths L2a and L2b of the second walls 419c and 420c.

As illustrated in FIG. 14, in plan view from the Z direction, the second wall 419c and the second wall 420c, which extend in parallel with the X direction, are disposed side by side in the X direction.

The second wall 419c is formed from the periphery of the opening 411A on the minus side in the X direction toward the plus side in the X direction, across a predetermined number of the suppression parts 43. The end portion of the second wall 419c on the minus side in the X direction is coupled with the periphery of the opening 411A on the minus side in the X direction, and the end portion of the second wall 419c on the plus side in the X direction is disposed opposite to the end portion of the second wall 420c on the minus side in the X direction, with a space therebetween.

The second wall 420c is formed from the periphery of the opening 411A on the plus side in the X direction toward the minus side in the X direction, across a predetermined number of the suppression parts 43. The end portion of the second wall 420c on the plus side in the X direction is coupled with the periphery of the opening 411A on the plus side in the X direction, and the end portion of the second wall 420c on the minus side in the X direction is disposed opposite to the end portion of the second wall 419c on the plus side in the X direction, with a space therebetween.

The distances from the end portions on the plus side in the X direction to the end portions on the minus side in the X direction in the second walls 419c and 420c are the lengths L2a and L2b of the second walls 419c and 420c, respectively. In this embodiment, the length L2a of the second wall 419c and the length L2b of the second wall 420c are substantially equal to each other, while the length L2a and the length L2b may be different from each other.

The width of the second wall 419c and the width of the second wall 420c are substantially equal to each other, and are the width W2. In addition, although not illustrated in the drawing, the height of the second wall 419c and the height of the second wall 420c are substantially equal to each other, and are the height H2.

The width W1 of the first wall 418c and the width W2 of the second walls 419c and 420c are substantially equal to each other. In addition, the height H1 of the first wall 418c and the height H2 of the second walls 419c and 420c are substantially equal to each other. In addition, the physical property of the first wall 418c and the physical property of the second walls 419c and 420c are substantially equal to each other.

According to this embodiment, effects similar to those of the embodiment 1 can be achieved. The lengths L2a and L2b of the second walls 419c and 420c are different from the length L1 of the first wall 418c, and thus the first wall 418c and the second walls 419c and 420c have resonance frequencies different from each other. As a result, when the vibration of the vibrating plate 412 is transmitted to the first wall 418c and the second walls 419c and 420c, the intensity of the resonance of each of the first wall 418c and the second walls 419c and 420c is small, and thus the generation of the vibration of unnecessary frequencies due to the resonance of the first wall 418c and the second walls 419c and 420c can be suppressed.

4. Embodiment 4

Next, a piezoelectric actuator 22d according to an embodiment 4 is described with reference to FIG. 15. Note that in the following description, differences from the above-described embodiment 1 are mainly described, the same configurations as those of the embodiment 1 are denoted with the same reference numerals, and overlapping descriptions are omitted.

In the piezoelectric actuator 22d according to this embodiment, the physical property of a first wall 418d and the physical property of a second wall 419d are different from each other. In this embodiment, the material of the first wall 418d and the material of the second wall 419d are different from each other, and thus the physical property of the first wall 418d and the physical property of the second wall 419d are made different from each other. For example, the Young's modulus of the first wall 418d and the Young's modulus of the second wall 419d can be made different from each other by forming the first wall 418d with silicon and forming the second wall 419d with a resin material such as acrylic resin and epoxy resin.

Figure 15:
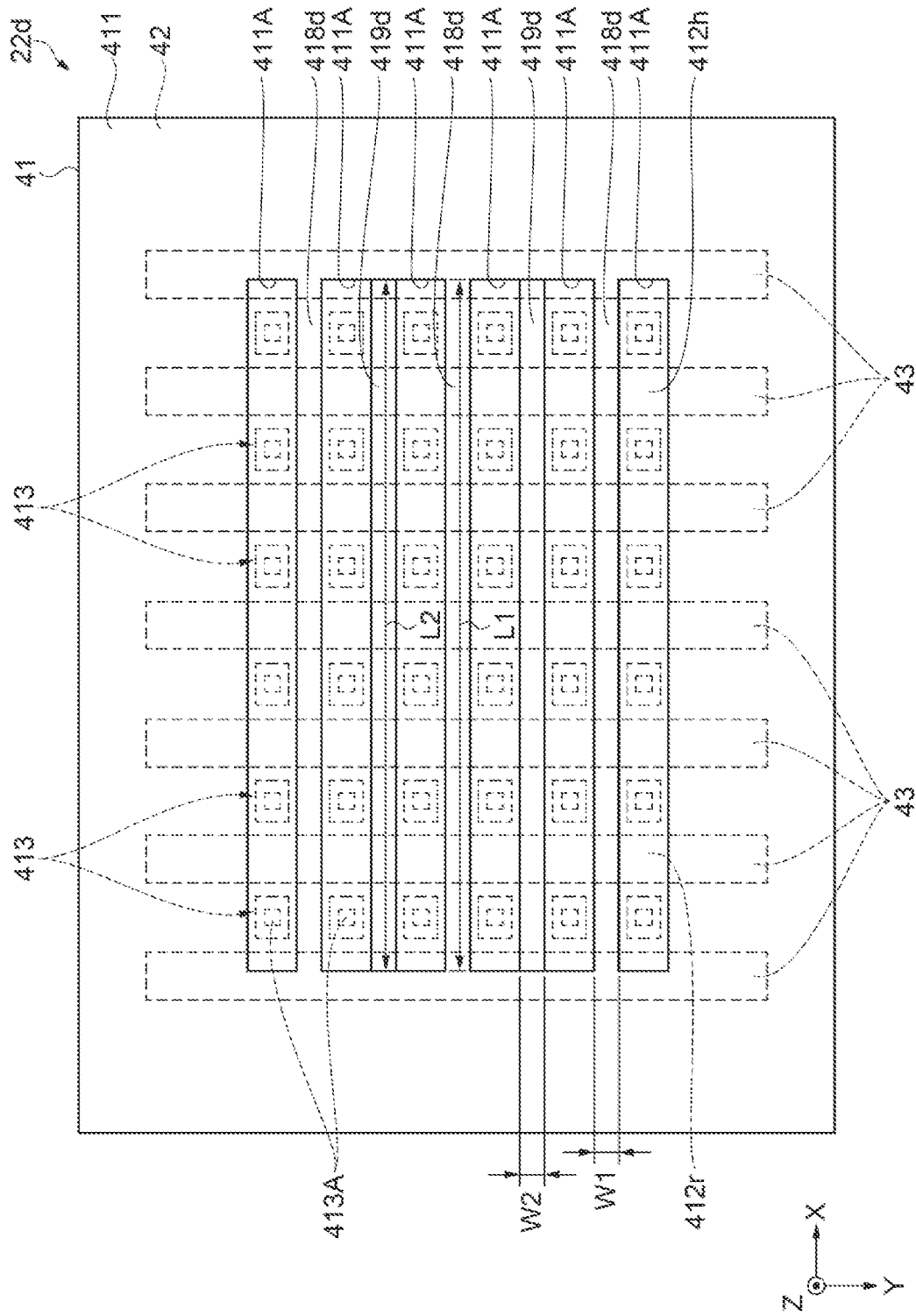
FIG. 15 is a plan view of a piezoelectric actuator according to an embodiment 4 as viewed from a base part side.

As illustrated in FIG. 15, the width W1 of the first wall 418d and the width W2 of the second wall 419d are substantially equal to each other. The length L1 of the first wall 418d and the length L2 of the second wall 419d are substantially equal to each other. In addition, although not illustrated in the drawing, the height H1 of the first wall 418d and the height H2 of the second wall 419d are substantially equal to each other.

In this embodiment, the first wall 418d can be formed by patterning the substrate 411 by a photolithography technique. The second wall 419d can be formed by applying a photosensitive resin material to the vibrating plate 412 by spin coating, sputtering or the like and then patterning it by a photolithography technique.

According to this embodiment, effects similar to those of the embodiment 1 can be achieved. The Young's modulus of the second wall 419d is different from the Young's modulus of the first wall 418d, and thus the first wall 418d and the second wall 419d have resonance frequencies different from each other. As a result, when the vibration of the vibrating plate 412 is transmitted to the first wall 418d and the second wall 419d, the intensity of the resonance of each of the first wall 418d and the second wall 419d is small, and thus the generation of the vibration of unnecessary frequencies due to the resonance of the first wall 418d and the second wall 419d can be suppressed.

Note that while the Young's modulus as an elastic modulus is exemplified as an example of the physical properties of the first wall 418d and the second wall 419d in this embodiment, physical properties other than the Young's modulus such as a modulus of rigidity and internal loss may also be used.

As described above, the widths W1 and W2 of the first wall 418 and the second wall 419 are different from each other in the embodiment 1, the heights H1 and H2 of the first wall 418b and the second wall 419b are different from each other in the embodiment 2, the length L1 of the first wall 418c and the lengths L2a and L2b of the second walls 419c and 420c are different from each other in the embodiment 3, and the physical properties of the first wall 418c and the second wall 419c are different from each other in the embodiment 4. In this manner, in the embodiments 1 to 4, the second wall is different from the first wall in one of the width, height, length, and physical property, but the second wall may be different from the first wall in two or more of the width, height, length, and physical property. In other words, by making the second wall different from the first wall in at least one of the width, height, length and physical property, effects similar to those of the embodiment 1 can be achieved.

5. Embodiment 5

Next, a piezoelectric actuator 22e according to an embodiment 5 is described with reference to FIG. 16. Note that in the following description, differences from the above-described embodiment 1 are mainly described, the same configurations as those of the embodiment 1 are denoted with the same reference numerals, and overlapping descriptions are omitted.

The piezoelectric actuator 22e of this embodiment is an example of an embodiment in which the first wall and the second wall are different from each other in two or more of the width, height, length and physical property, and a first wall 418e and a second wall 419e are different from each other in the widths W1 and W2 and the physical property.

Figure 16:
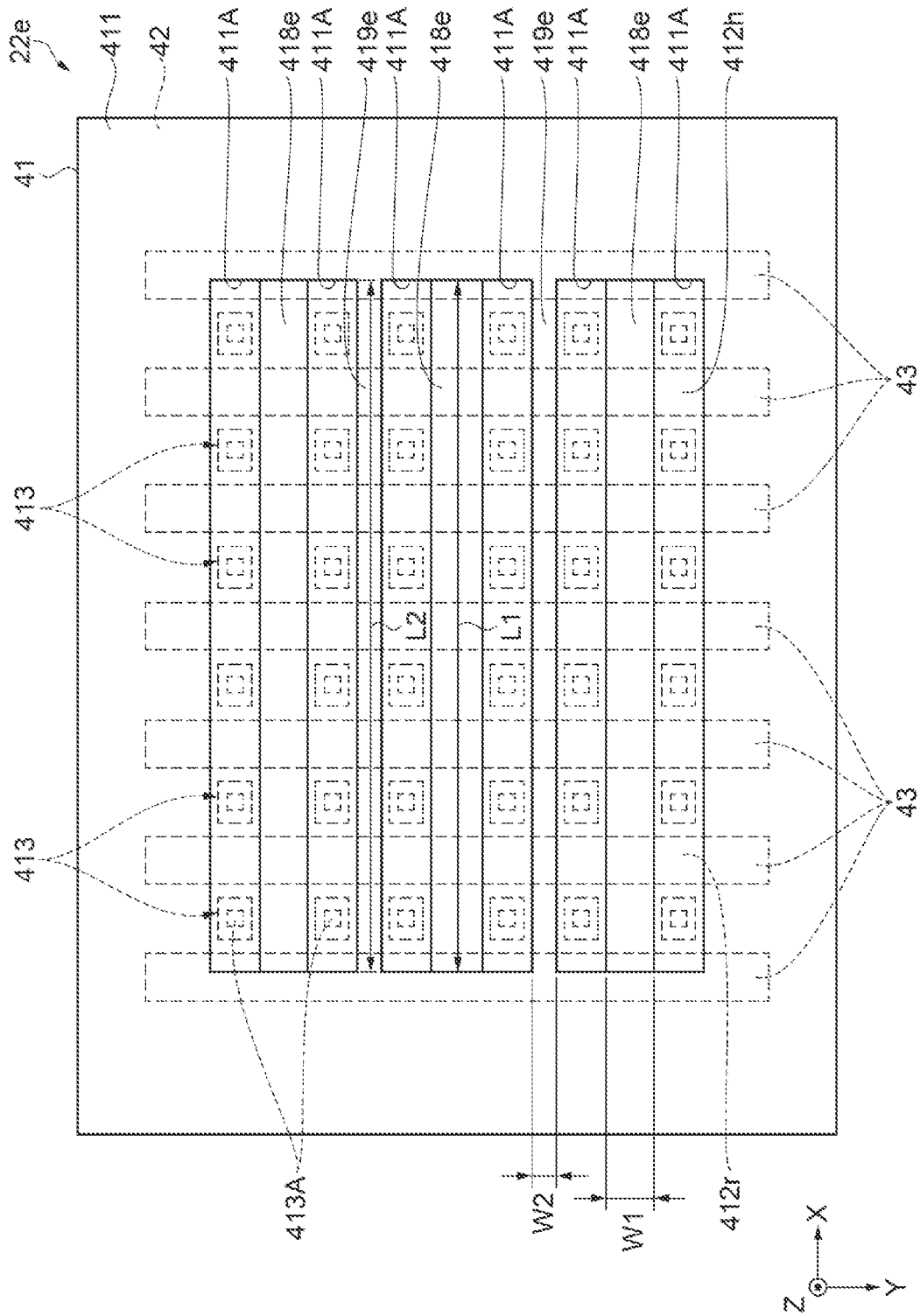
FIG. 16 is a plan view of a piezoelectric actuator according to an embodiment 5 as viewed from a base part side.

As illustrated in FIG. 16, in the piezoelectric actuator 22e, the width W1 of the first wall 418e and the width W2 of the second wall 419e are different from each other.

Further, in this embodiment, the first wall 418e is formed with silicon and the second wall 419e is formed with a resin material, and thus, the Young's modulus of the first wall 418e and the Young's modulus of the second wall 419e are different from each other.

The length L1 of the first wall 418e and the length L2 of the second wall 419e are substantially equal to each other. In addition, although not illustrated in the drawing, the height H1 of the first wall 418e and the height H2 of the second wall 419e are substantially equal to each other.

According to this embodiment, effects similar to those of the embodiment 1 can be achieved. The width W2 and Young's modulus of the second wall 419e are different from the width W1 and Young's modulus of the first wall 418e, and thus the first wall 418e and the second wall 419e have resonance frequencies different from each other. As a result, when the vibration of the vibrating plate 412 is transmitted to the first wall 418e and the second wall 419e, the intensity of the resonance of each of the first wall 418e and the second wall 419e is small, and thus the generation of the vibration of unnecessary frequencies due to the resonance of the first wall 418e and the second wall 419e can be suppressed.

6. Embodiment 6

Next, a piezoelectric actuator 22f according to an embodiment 6 is described with reference to FIG. 17 and FIG. 18. Note that in the following description, differences from the above-described embodiment 1 are mainly described, the same configurations as those of the embodiment 1 are denoted with the same reference numerals, and overlapping descriptions are omitted.

The piezoelectric actuator 22f according to this embodiment is an example of an embodiment in which the first wall and the second wall are different from each other in two or more of the width, height, length and physical property, and a first wall 418f and second walls 419f and 420f are different from each other in the height, length and physical property.

Figure 17:
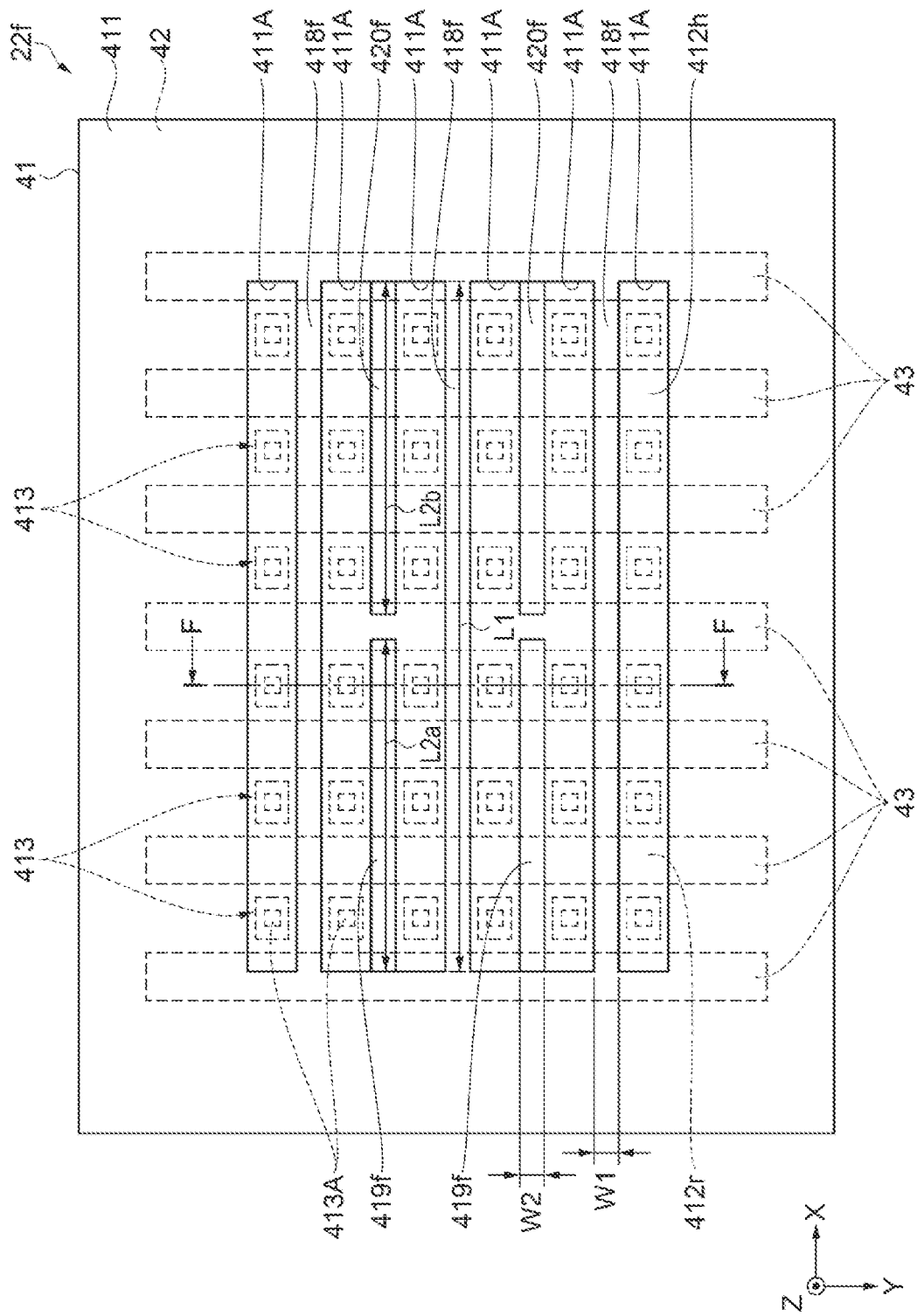
FIG. 17 is a plan view of a piezoelectric actuator according to an embodiment 6 as viewed from a base part side.

As illustrated in FIG. 17, in plan view from the Z direction, the second wall 419f and the second wall 420f, which extend in parallel with the X direction, are disposed side by side in the X direction. The end portion of the second wall 419f on the minus side in the X direction is coupled with the periphery of the opening 411A on the minus side in the X direction, the end portion of the second wall 420f on the plus side in the X direction is coupled with the periphery of the opening 411A on the plus side in the X direction, and the end portion of the second wall 419f on the plus side in the X direction and the end portion of the second wall 420f on the minus side in the X direction are disposed opposite to each other with a space therebetween.

The width of the second wall 419f and the width of the second wall 420f are substantially equal to each other, and are the width W2. The width W2 of the second walls 419f and 420f and the width W1 of the first wall 418f are substantially equal to each other.

Although not illustrated in the drawing, the height of the second wall 419f and the height of the second wall 420f are substantially equal to each other, and are the height H2.

Figure 18:
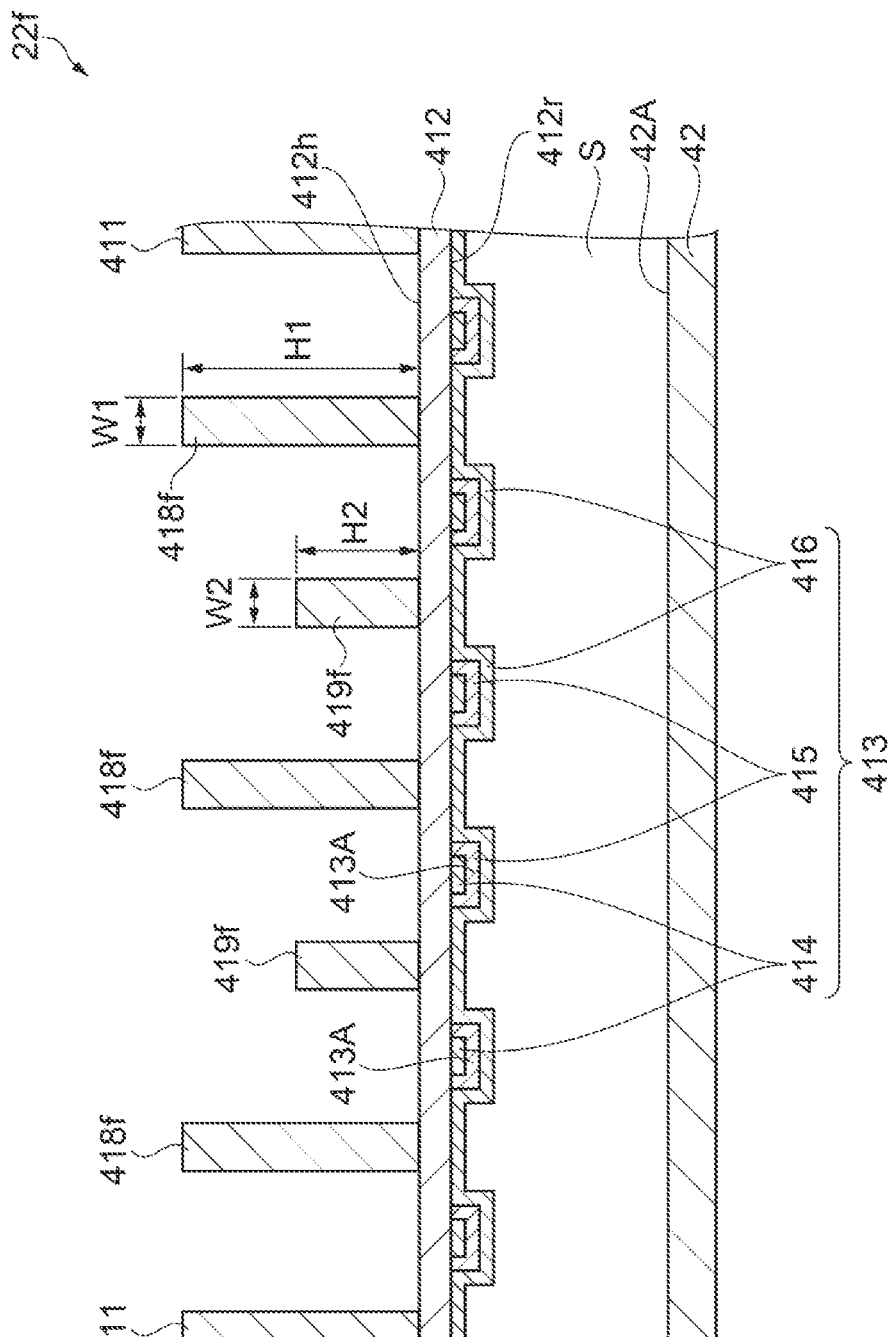
FIG. 18 is a sectional view taken along a line F-F in FIG. 17.

As illustrated in FIG. 18, the height H1 of the first wall 418f and the height H2 of the second walls 419f and 420f are different from each other. More specifically, the height H1 of the first wall 418f are greater than the height H2 of the second walls 419f and 420f.

As illustrated in FIG. 17, the distances from the end portion on the plus side in the X direction to the end portion on the minus side in the X direction in the second walls 419f and 420f are the lengths L2a and L2b of the second walls 419f and 420f, respectively.

The length L1 of the first wall 418f and the lengths L2a and L2b of the second walls 419f and 420f are different from each other. More specifically, the length L1 of the first wall 418f is greater than the lengths L2a and L2b of the second walls 419f and 420f.

Further, in this embodiment, the first wall 418f is formed with silicon, the second walls 419f and 420f are formed with a resin material, and thus the Young's modulus of the first wall 418f and the Young's modulus of the second walls 419f and 420f are different from each other.

According to this embodiment, effects similar to those of the embodiment 1 can be achieved. The height H2, the lengths L2a and L2b, and Young's modulus as an example of the physical property of the second walls 419f and 420f are different from the height H1, length L1 and Young's modulus of the first wall 418f, and thus the first wall 418f and the second walls 419f and 420f have resonance frequencies different from each other. As a result, when the vibration of the vibrating plate 412 is transmitted to the first wall 418f and the second walls 419f and 420f, the intensity of the resonance of each of the first wall 418f and the second walls 419f and 420f is small, and thus the generation of the vibration of unnecessary frequencies due to the resonance of the first wall 418f and the second walls 419f and 420f can be suppressed.

7. Embodiment 7

Next, a piezoelectric actuator 22g according to an embodiment 7 is described with reference to FIG. 19 to FIG. 21. Note that in the following description, differences from the above-described embodiment 1 are mainly described, the same configurations as those of the embodiment 1 are denoted with the same reference numerals, and overlapping descriptions are omitted.

The piezoelectric actuator 22g according to this embodiment is different from the piezoelectric actuator 22 of the embodiment 1 in that, in plan view from the Z direction, a plurality of suppression parts 43A extending in parallel with the Y direction and a plurality of suppression parts 43B extending in parallel with the X direction are provided.

Figure 19:
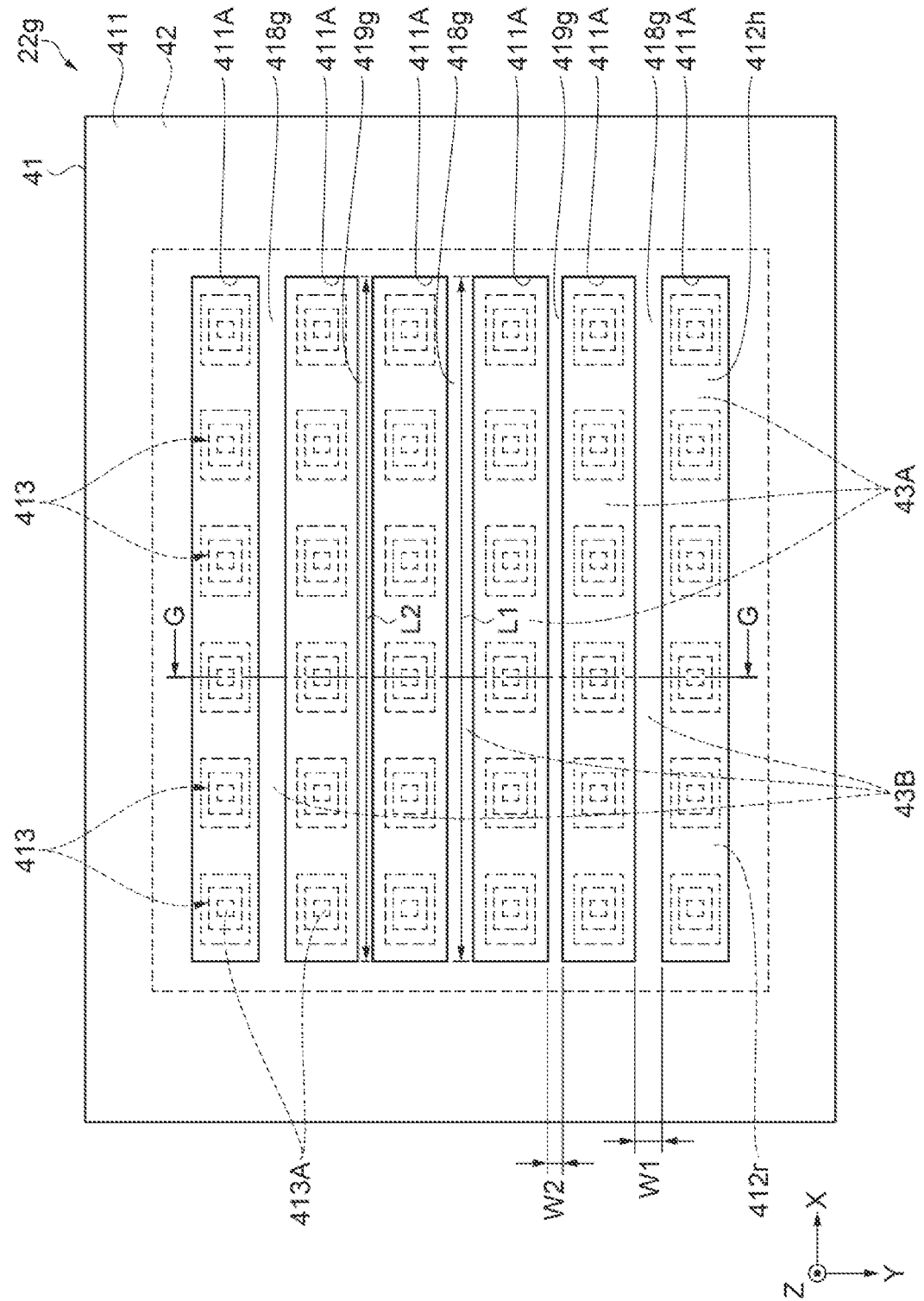
FIG. 19 is a plan view of a piezoelectric actuator according to an embodiment 7 as viewed from a base part side.
Figure 20:
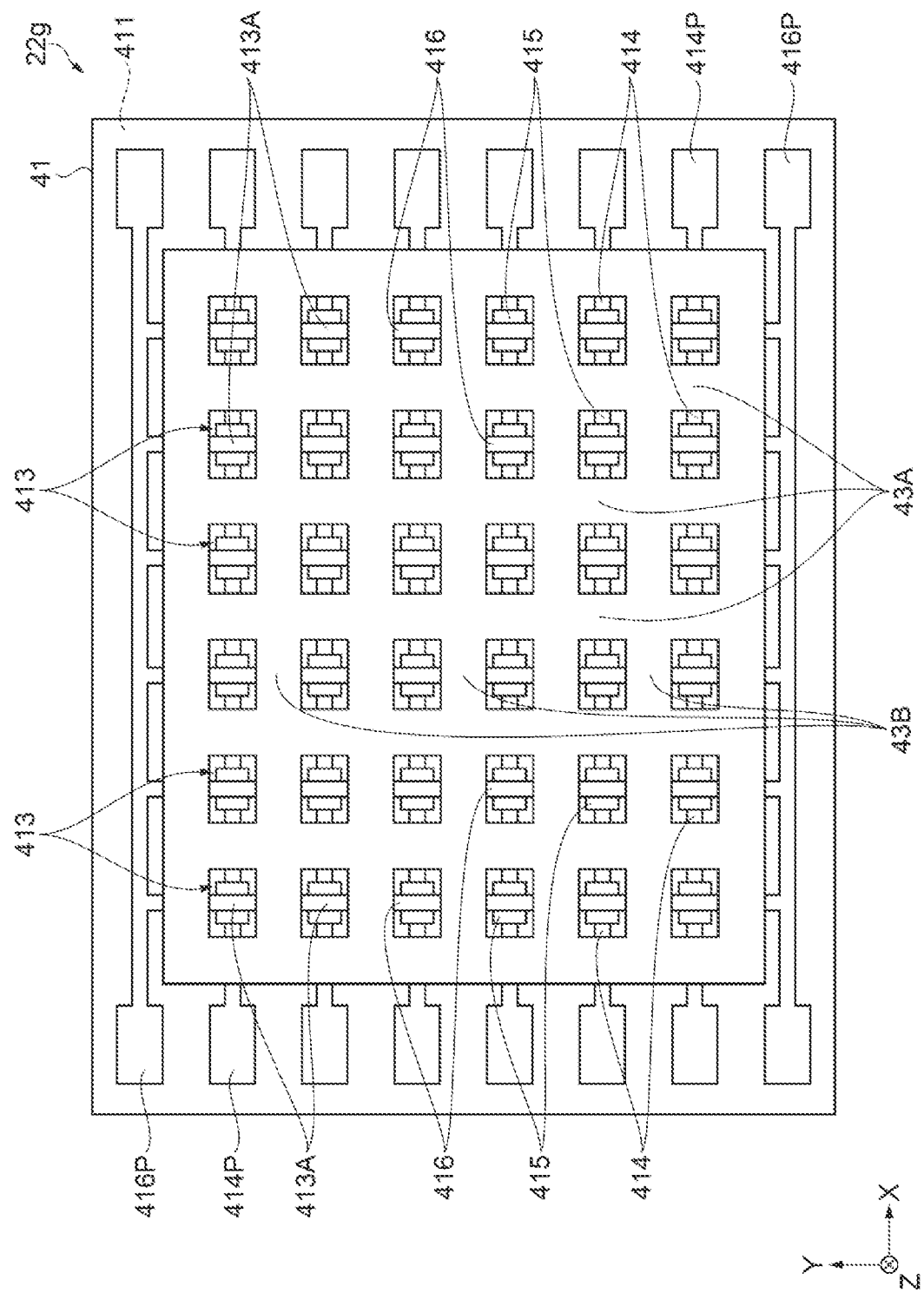
FIG. 20 is a plan view of the piezoelectric actuator according to the embodiment 7 as viewed from a sealing plate side.

As illustrated in FIG. 19 and FIG. 20, the suppression parts 43A and 43B are provided corresponding to the active part 413A.

In plan view from the Z direction, the suppression part 43A extends in parallel with the Y direction. The plurality of suppression parts 43A is disposed side by side in the X direction. The plurality of piezoelectric elements 413 is disposed side by side in the Y direction between the plurality of suppression parts 43A. In other words, in plan view from the Z direction, the suppression part 43A is provided to sandwich the active part 413A in the X direction.

In plan view from the Z direction, the suppression part 43B extends in parallel with the X direction. The plurality of suppression parts 43B is disposed side by side in the Y direction. The plurality of piezoelectric elements 413 is disposed side by side in the X direction between the plurality of suppression parts 43B. In other words, in plan view from the Z direction, the suppression part 43B is provided to sandwich the active part 413A in the Y direction.

That is, the suppression part 43A is disposed on the plus side in the X direction and the minus side in the X direction of the active part 413A at the vibrating plate 412, and the suppression part 43B is disposed on the plus side in the Y direction and the minus side in the Y direction of the active part 413A at the vibrating plate 412. In this manner, with the suppression part 43A and the suppression part 43B, the vibration range of the vibrating plate 412 in the X direction and the Y direction can be limited.

Figure 21:
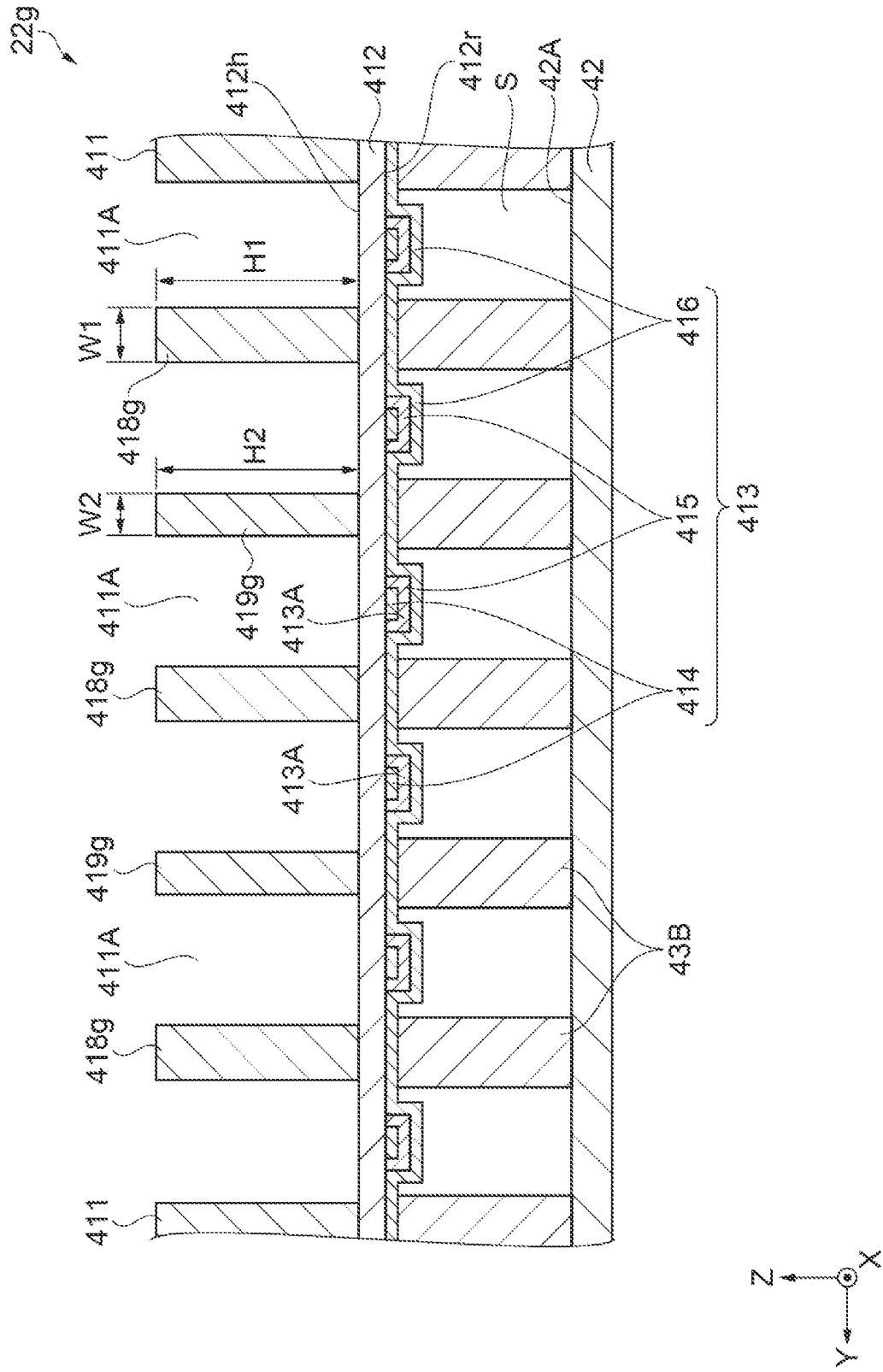
FIG. 21 is a sectional view taken along a line G-G in FIG. 19.

As illustrated in FIG. 19, the length L1 of a first wall 418g and the length L2 of a second wall 419g are substantially equal to each other, and as illustrated in FIG. 21, the height H1 of the first wall 418g and the height H2 of the second wall 419g are substantially equal to each other. As illustrated in FIG. 19 and FIG. 21, the width W1 of the first wall 418g and the width W2 of the second wall 419g are different from each other. More specifically, the width W1 of the first wall 418g is greater than the width W2 of the second wall 419g.

According to this embodiment, effects similar to those of the embodiment 1 can be achieved. The width W2 of the second wall 419g is different from the width W1 of the first wall 418g, and thus the first wall 418g and the second wall 419g have resonance frequencies different from each other. As a result, when the vibration of the vibrating plate 412 is transmitted to the first wall 418g and the second wall 419g, the intensity of the resonance of each of the first wall 418g and the second wall 419g is small, and thus the generation of the vibration of unnecessary frequencies due to the resonance of the first wall 418g and the second wall 419g can be suppressed.

8. Embodiment 8

Next, a piezoelectric actuator 22h according to an embodiment 8 is described with reference to FIG. 22 and FIG. 23. Note that in the following description, differences from the above-described embodiment 7 are mainly described, the same configurations as those of the embodiment 7 are denoted with the same reference numerals, and overlapping descriptions are omitted.

Figure 23:
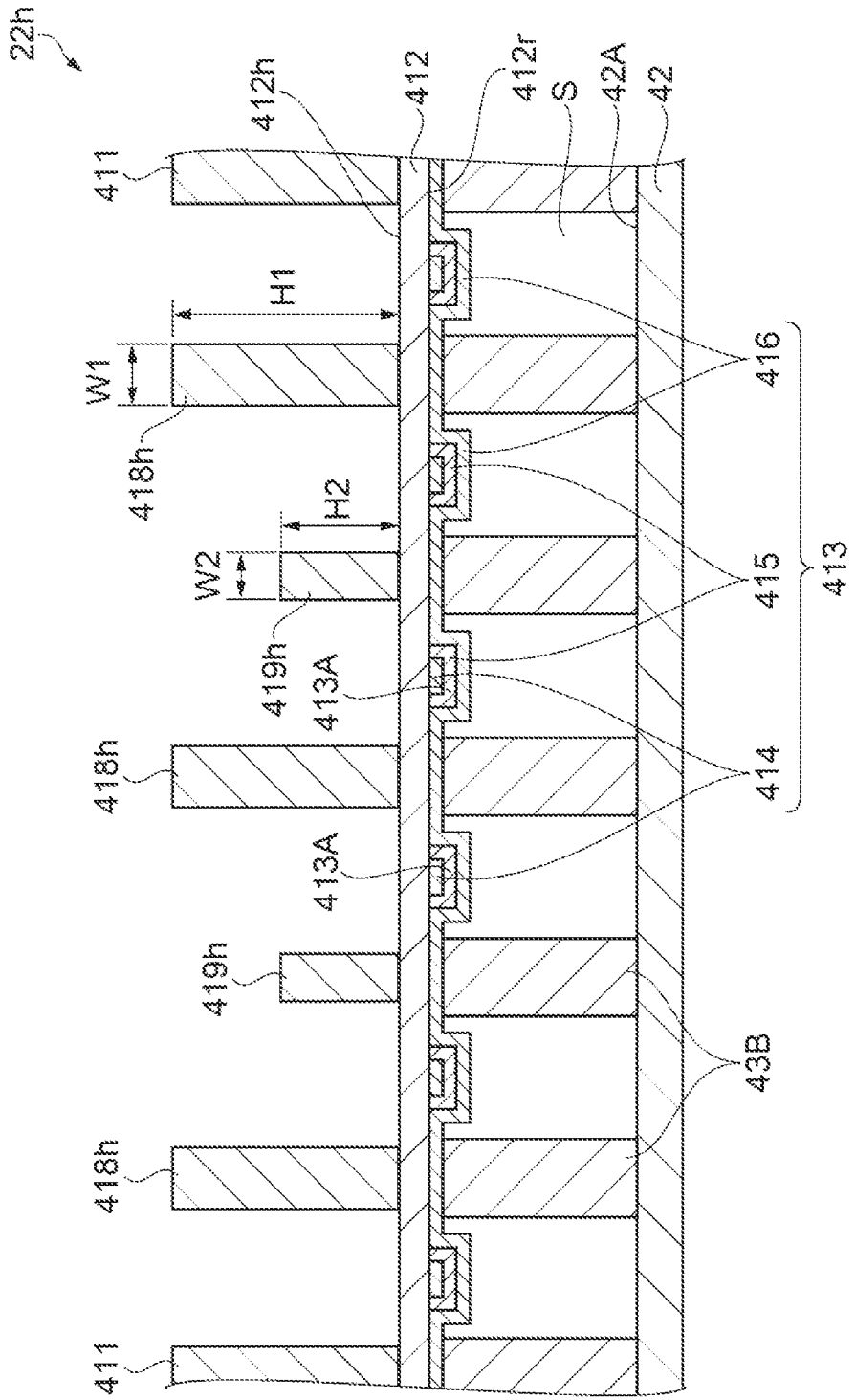
FIG. 23 is a sectional view taken along a line H-H in FIG. 22.

As illustrated in FIG. 23, in the piezoelectric actuator 22h according to this embodiment, the height H1 of a first wall 418h and the height H2 of a second wall 419h are different from each other. More specifically, the height H1 of the first wall 418h is greater than the height H2 of the second wall 419h.

Figure 22:
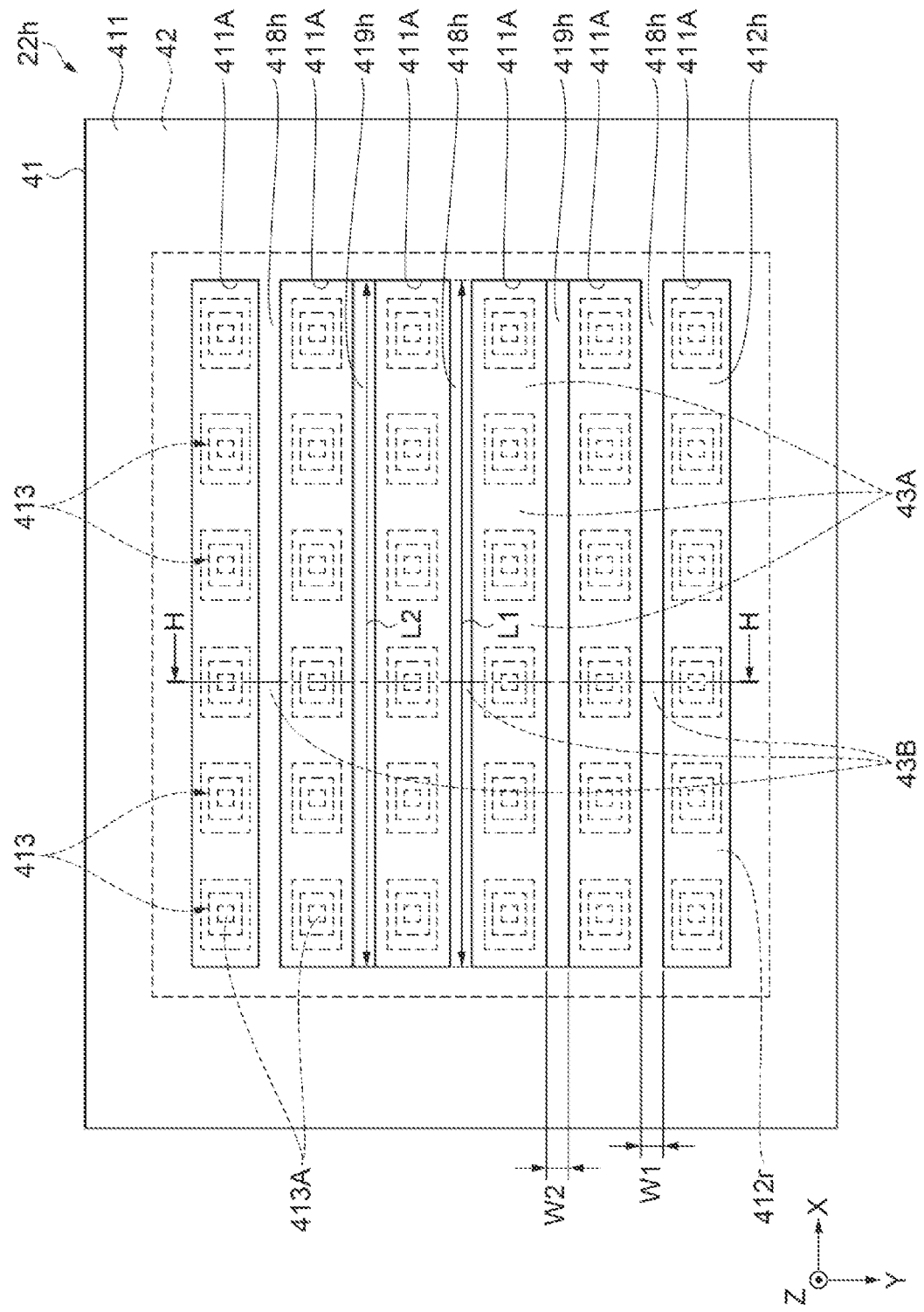
FIG. 22 is a plan view of a piezoelectric actuator according to an embodiment 8 as viewed from a base part side.

As illustrated in FIG. 22, in this embodiment, the width W1 of the first wall 418h and the width W2 of the second wall 419h are substantially equal to each other, and the length L1 of the first wall 418h and the length L2 of the second wall 419h are substantially equal to each other.

According to this embodiment, effects similar to those of the embodiment 1 can be achieved. The height H2 of the second wall 419h is different from the height H1 of the first wall 418h, and thus the first wall 418h and the second wall 419h have resonance frequencies different from each other. As a result, when the vibration of the vibrating plate 412 is transmitted to the first wall 418h and the second wall 419h, the intensity of the resonance of each of the first wall 418h and the second wall 419h is small, and thus the generation of the vibration of unnecessary frequencies due to the resonance of the first wall 418h and the second wall 419h can be suppressed.

9. Embodiment 9

Next, a piezoelectric actuator 22k according to an embodiment 9 is described with reference to FIG. 24. Note that in the following description, differences from the above-described embodiment 7 are mainly described, the same configurations as those of the embodiment 7 are denoted with the same reference numerals, and overlapping descriptions are omitted.

Figure 24:
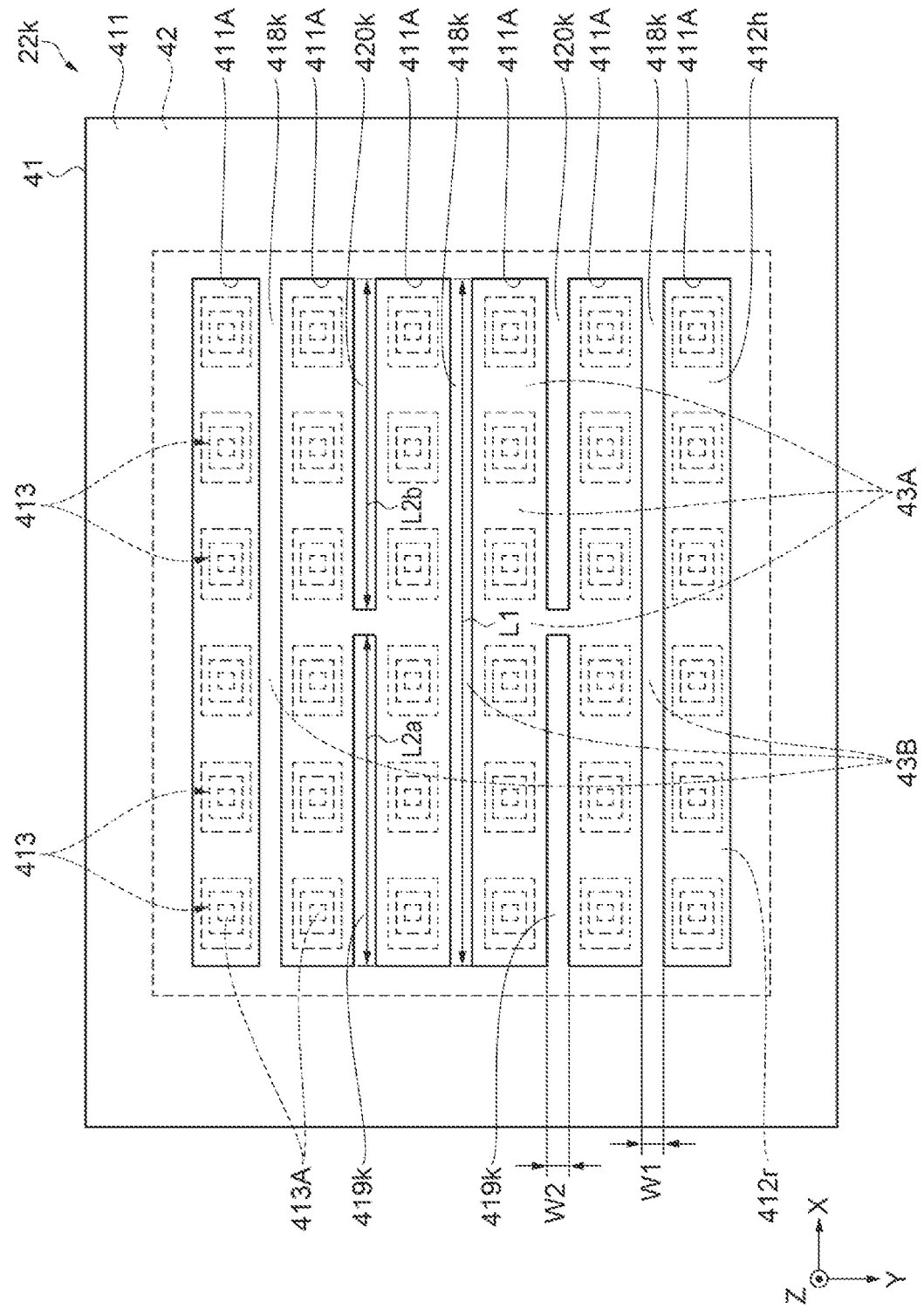
FIG. 24 is a plan view of a piezoelectric actuator according to an embodiment 9 as viewed from a base part side.

As illustrated in FIG. 24, in the piezoelectric actuator 22k according to this embodiment, the length L1 of a first wall 418k and the lengths L2a and L2b of second walls 419k and 420k are different from each other. More specifically, the length L1 of the first wall 418k is greater than the lengths L2a and L2b of the second walls 419k and 420k.

As illustrated in FIG. 24, in plan view from the Z direction, the second wall 419k and the second wall 420k, which extend in parallel with the X direction, are disposed side by side in the X direction. The end portion of the second wall 419k on the minus side in the X direction is coupled with the periphery of the opening 411A on the minus side in the X direction, the end portion of the second wall 420k on the plus side in the X direction is coupled with the periphery of the opening 411A on the plus side in the X direction, and the end portion of the second wall 419k on the plus side in the X direction and the end portion of the second wall 420k on the minus side in the X direction are disposed opposite to each other with a space therebetween.

The distances from the end portions on the plus side in the X direction to the end portion on the minus side in the X direction in the second walls 419k and 420k are the lengths L2a and L2b of the second walls 419k and 420k, respectively.

The width of the second wall 419k and the width of the second wall 420k are substantially equal to each other, and are the width W2. The widths W2 of the second walls 419k and 420k and the width W1 of the first wall 418k are substantially equal to each other. In addition, although not illustrated in the drawing, the height of the second wall 419k and the height of the second wall 420k are substantially equal to each other, and are the height H2. The heights H2 of the second walls 419k and 420k and the height H1 of the first wall 418k are substantially equal to each other.

According to this embodiment, effects similar to those of the embodiment 1 can be achieved. The lengths L2a and L2b of the second walls 419k and 420k are different from the length L1 of the first wall 418k, and thus the first wall 418k and the second walls 419k and 420k have resonance frequencies different from each other. As a result, when the vibration of the vibrating plate 412 is transmitted to the first wall 418k and the second walls 419k and 420k, the intensity of the resonance of each of the first wall 418k and the second walls 419k and 420k is small, and thus the generation of the vibration of unnecessary frequencies due to the first wall 418k and the second walls 419k and 420k the resonance of can be suppressed.

10. Embodiment 10

Figure 25:
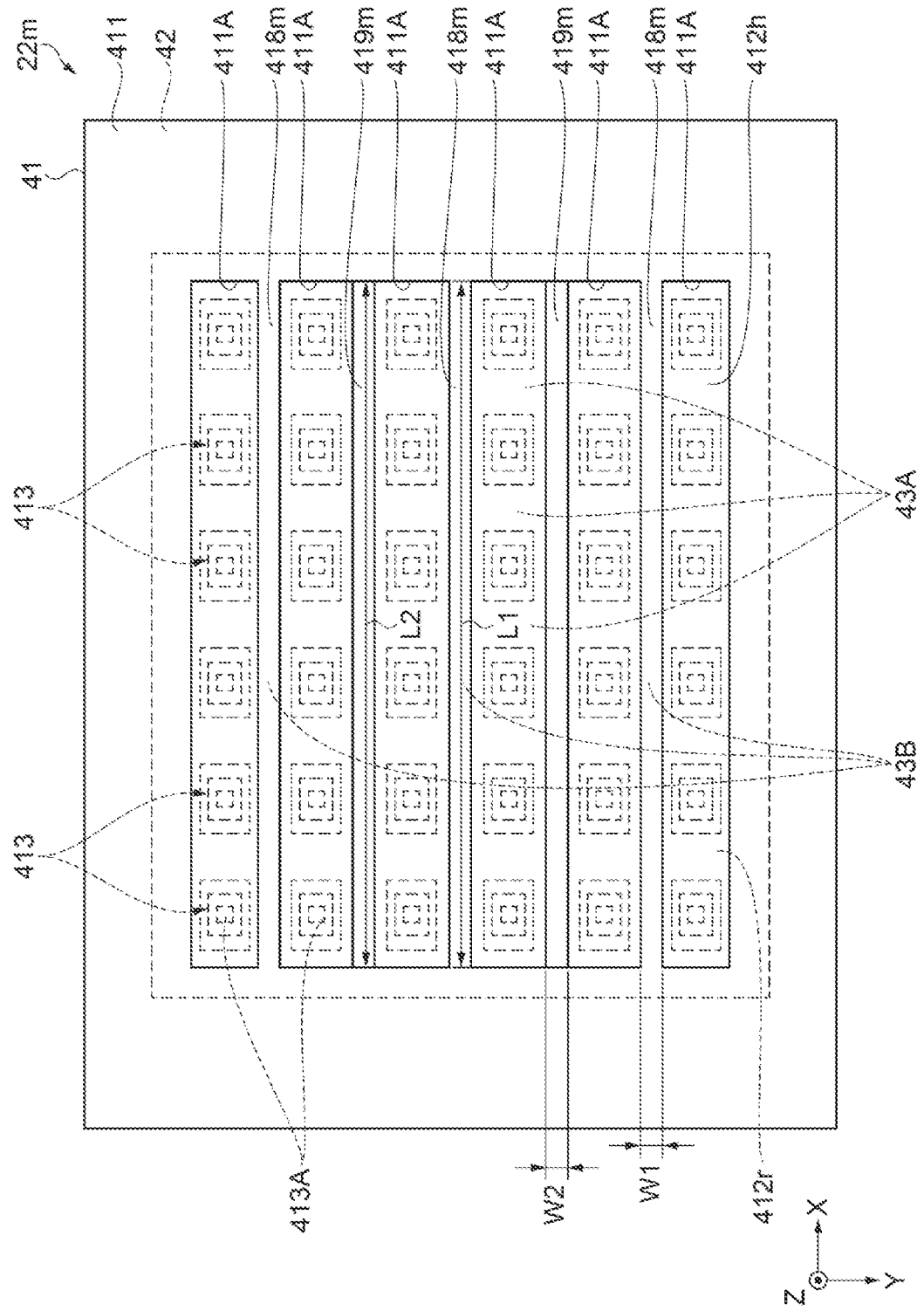
FIG. 25 is a plan view of a piezoelectric actuator according to an embodiment 10 as viewed from a base part side.

Next, a piezoelectric actuator 22m according to an embodiment 10 is described with reference to FIG. 25. Note that in the following description, differences from the above-described embodiment 7 are mainly described, the same configurations as those of the embodiment 7 are denoted with the same reference numerals, and overlapping descriptions are omitted.

In the piezoelectric actuator 22m according to this embodiment, the physical property of a first wall 418m and the physical property of a second wall 419m are different from each other. In this embodiment, the first wall 418m is formed with silicon and the second wall 419m is formed with a resin material, and thus, the Young's modulus of the first wall 418m and the Young's modulus of the second wall 419m are different from each other.

In this embodiment, the first wall 418m is formed with silicon and the second wall 419m is formed with a resin material, and thus, the Young's modulus of the first wall 418m and the Young's modulus of the second wall 419m are different from each other. The length L1 of the first wall 418m and the length L2 of the second wall 419m are substantially equal to each other. In addition, although not illustrated in the drawing, the height H1 of the first wall 418m and the height H2 of the second wall 419m are substantially equal to each other.

According to this embodiment, effects similar to those of the embodiment 1 can be achieved. The Young's modulus of the second wall 419m is different from the Young's modulus of the first wall 418m, and thus the first wall 418m and the second wall 419m have resonance frequencies different from each other. As a result, when the vibration of the vibrating plate 412 is transmitted to the first wall 418m and the second wall 419m, the intensity of the resonance of each of the first wall 418m and the second wall 419m is small, and thus the generation of the vibration of unnecessary frequencies due to the resonance of the first wall 418m and the second wall 419m can be suppressed.

What is claimed is:

1. A piezoelectric actuator comprising:
   a substrate in which an opening is formed, the opening extending along a first direction in a plan view;
   a vibrating plate having a first surface and a second surface outwardly opposite to each other, the first surface closing the opening;
   a piezoelectric element provided, corresponding to the opening, at the second surface of the vibrating plate;
   a sealing plate disposed on the second surface of the vibrating plate;
   a suppression part configured to suppress a vibration of the vibrating plate, the suppression part being formed in the sealing plate, the suppression part being configured with a plurality of suppression walls extending along a second direction different from the first direction in the plan view, each of the plurality of suppression walls being sandwiched by two through-holes disposed in the sealing plate, each of the through-holes housing the piezoelectric element;
   a first wall protruding from a first position of the first surface into the opening along a third direction different from the first and second directions; and
   a second wall protruding from a second position of the first surface into the opening along the third direction, wherein
   in the piezoelectric element, a first electrode, a piezoelectric layer, and a second electrode are stacked in this order from a side of the second surface,
   when a portion where the first electrode, the piezoelectric layer, and the second electrode overlap each other is defined as an active part, the first wall and the second wall are provided to sandwich the active part in the plan view, and
   the second wall is different from the first wall at least in one of a width along the second direction, a length along the first direction, and a physical property with respect to materials of the first and second walls.

2. The piezoelectric actuator according to claim 1, wherein the suppression part is provided at the second surface of the vibrating plate.

3. An ultrasound element comprising:
   the piezoelectric actuator according to claim 2;
   a transmission circuit configured to cause the piezoelectric actuator to transmit ultrasound waves; and
   a reception circuit configured to cause the piezoelectric actuator to receive ultrasound waves.

4. An ultrasound probe comprising:
   the ultrasound element according to claim 3; and
   a housing configured to house the ultrasound element.

5. An ultrasound device comprising:
   the ultrasound element according to claim 3; and
   a controller configured to control the ultrasound element.

6. An electronic device comprising the piezoelectric actuator according to claim 2.

7. An ultrasound element comprising:
   the piezoelectric actuator according to claim 1;
   a transmission circuit configured to cause the piezoelectric actuator to transmit ultrasound waves; and
   a reception circuit configured to cause the piezoelectric actuator to receive ultrasound waves.

8. An ultrasound probe comprising:
   the ultrasound element according to claim 7; and
   a housing configured to house the ultrasound element.

9. An ultrasound device comprising:
   the ultrasound element according to claim 7; and
   a controller configured to control the ultrasound element.

10. An electronic device comprising the piezoelectric actuator according to claim 1.

* * * * *